US012624992B2

(12) United States Patent
Schiffman

(10) Patent No.: US 12,624,992 B2
(45) Date of Patent: May 12, 2026

(54) CUSTOMIZED UV RADIATION EXPOSURE NOTIFICATION APPARATUS, SYSTEM, AND METHOD

(71) Applicant: Kristina Schiffman, Park City, UT (US)

(72) Inventor: Kristina Schiffman, Park City, UT (US)

(73) Assignee: Kristina Schiffman, Park City, UT (US)

( * ) Notice: Subject to any disclaimer, the term of this patent is extended or adjusted under 35 U.S.C. 154(b) by 213 days.

(21) Appl. No.: 18/638,461

(22) Filed: Apr. 17, 2024

(65) Prior Publication Data

US 2025/0327705 A1     Oct. 23, 2025

Related U.S. Application Data

(60) Provisional application No. 63/496,526, filed on Apr. 17, 2023.

(51) Int. Cl.
| | |
|---|---|
| *A61B 5/00* | (2006.01) |
| *G01J 1/02* | (2006.01) |
| *G01J 1/42* | (2006.01) |
| *G16H 40/67* | (2018.01) |
| *G16H 50/30* | (2018.01) |

(52) U.S. Cl.
CPC ............ *G01J 1/429* (2013.01); *A61B 5/0064* (2013.01); *A61B 5/441* (2013.01); *A61B 5/6831* (2013.01); *G01J 1/0219* (2013.01); *G16H 40/67* (2018.01); *G16H 50/30* (2018.01); *G01J 2001/4266* (2013.01)

(58) Field of Classification Search
CPC ..... A61B 5/0064; A61B 5/441; A61B 5/6831; G01J 1/0219; G01J 1/429; G01J 2001/4266; G16H 40/67; G16H 50/30
See application file for complete search history.

(56) References Cited

U.S. PATENT DOCUMENTS

| | | | |
|---|---|---|---|
| 5,387,798 A | 2/1995 | Funakoshi et al. | |
| 9,662,062 B2 * | 5/2017 | De Guia | G01J 1/4228 |

(Continued)

FOREIGN PATENT DOCUMENTS

| | | |
|---|---|---|
| CN | 108472499 A | 8/2018 |
| CN | 109348407 A | 2/2019 |

(Continued)

*Primary Examiner* — Mark R Gaworecki
(74) *Attorney, Agent, or Firm* — Alexis V. Nelson

(57)     ABSTRACT

An apparatus for monitoring UV radiation exposure and notifying a user of a risk of overexposure is disclosed. The apparatus receives physical characteristic input for a user, as well as a current UV radiation level and an exposure time for at least one area of the user's body. Body mapping data is generated, and a UV exposure risk for each area is assessed based on the input and the body mapping data. A threshold UV radiation exposure value for each area is determined based on the UV exposure risk. A current UV radiation exposure value is determined based on the current UV radiation level input. The current UV radiation exposure value is compared to the threshold UV radiation exposure value to generate UV radiation exposure data. The user is notified of a remaining time for UV radiation exposure based on the UV radiation exposure data.

20 Claims, 16 Drawing Sheets

(56)  References Cited

U.S. PATENT DOCUMENTS

| | | | |
|---|---|---|---|
| 10,132,680 | B1 | 11/2018 | Isikman et al. |
| 10,561,376 | B1 * | 2/2020 | Kahn ...................... G01J 1/429 |
| 11,118,968 | B1 * | 9/2021 | Lian .......................... G01T 1/02 |
| 2006/0289779 | A1 | 12/2006 | Marmaropoulos |
| 2014/0278139 | A1 * | 9/2014 | Hong ................... A61B 5/1118 |
| | | | 702/19 |
| 2014/0288396 | A1 | 9/2014 | LeBoeuf et al. |
| 2015/0177059 | A1 | 6/2015 | Lian et al. |
| 2016/0305819 | A1 * | 10/2016 | Lian ........................ G01J 1/429 |
| 2016/0313176 | A1 | 10/2016 | Lee |
| 2017/0069192 | A1 * | 3/2017 | Sood ................ H04M 1/72454 |
| 2019/0017866 | A1 | 1/2019 | Sood et al. |
| 2019/0033126 | A1 * | 1/2019 | Dumont ............... G01J 1/0228 |
| 2019/0060678 | A1 | 2/2019 | Poutiatine |
| 2019/0145820 | A1 | 5/2019 | Dumont et al. |
| 2019/0204146 | A1 * | 7/2019 | Wei ....................... G01J 1/0209 |
| 2020/0107772 | A1 * | 4/2020 | Hu ........................ G01J 1/0228 |
| 2020/0112659 | A1 * | 4/2020 | Hu ........................ G01J 1/0228 |
| 2022/0057260 | A1 | 2/2022 | Dumont et al. |
| 2022/0079521 | A1 * | 3/2022 | Grena ....................... G01J 1/42 |

FOREIGN PATENT DOCUMENTS

| | | | | |
|---|---|---|---|---|
| JP | 5524678 | A | 2/1980 | |
| KR | 20180090902 | A | 8/2018 | |
| WO | 2015051013 | A1 | 4/2015 | |
| WO | 2017120176 | A1 | 7/2017 | |
| WO | 2018208166 | A3 | 11/2018 | |
| WO | WO-2019036589 | A1 * | 2/2019 | ........... G01J 1/0219 |

* cited by examiner

CUSTOMIZED UV RADIATION EXPOSURE NOTIFICATION APPARATUS, SYSTEM, AND METHOD

FIELD

This invention relates to health monitoring devices and more particularly relates to a device for monitoring exposure to ultraviolet radiation.

BACKGROUND

Ultraviolet (UV) radiation exposure poses significant health risks to individuals, including the potential for sunburn, skin cancer, and premature aging of the skin. Prolonged exposure to UV radiation, particularly at high levels, can have detrimental effects on human health. Therefore, it is essential for individuals to be aware of their UV radiation exposure levels and take appropriate measures to mitigate risks.

Existing methods for monitoring UV radiation exposure tend to rely on subjective assessments or intermittent measurements using standalone devices. These methods may not provide real-time feedback or personalized recommendations based on individual characteristics and environmental conditions.

SUMMARY

An apparatus for monitoring UV radiation exposure and notifying a user of a risk of overexposure is disclosed. A system and method also perform the functions of the apparatus.

The apparatus may include one or more processors and non-transitory computer-readable storage media storing code executable by the processors to perform operations. The operations include receiving physical characteristic input including at least one physical characteristic of a user. The operations further include receiving, from a UV light sensor assembly, a current UV radiation level input including a current UV radiation level and an exposure time corresponding to at least one of multiple areas of the user's body. The operations further include generating body mapping data for the user based on the physical characteristic input and the current UV radiation level input, and assessing a UV exposure risk for each of the areas based on the physical characteristic input, the current UV radiation level input, and the body mapping data. A threshold radiation exposure value for each of the areas is determined based on the UV exposure risk.

The operations further include determining a current UV radiation exposure value for at least one of the areas based on the current UV radiation level input. The operations further include comparing the current UV radiation exposure value to the threshold UV radiation exposure value for at least one area and generating UV radiation exposure data based thereon. The operations further include notifying the user of a remaining time for UV radiation exposure of the area based on the UV radiation exposure data.

In some embodiments, the operations further iteratively detecting the current UV radiation exposure radiation level and the exposure time at predetermined periodic intervals and updating the remaining time for UV exposure based on the detection.

According to another aspect of the present disclosure, the system includes a wearable ultraviolet light sensor configured to detect a current ultraviolet (UV) radiation level and an exposure time corresponding to at least one of multiple areas of a user's body. The UV light sensor assembly is configured to be worn by a user in at least one of the areas, and the exposure time indicates an amount of time that the area has been exposed to UV radiation.

The system further includes a computing device having a processor in communication with the wearable UV light sensor assembly. The processor is configured to receive input regarding at least one physical characteristic of the user. The processor is further configured to receive body mapping data for the user and to assess a UV exposure risk for each of a plurality of areas of the user's body based on the input and the body mapping data. The processor is configured to determine, based on the UV exposure risk, a threshold UV radiation exposure value for each area. The processor is further configured to determine a current UV radiation exposure value for the area based on the current UV radiation level and the exposure time. The current UV radiation exposure value is compared to the threshold UV radiation exposure value for the area and UV radiation exposure data is generated based thereon. The processor is configured to notify the user of a remaining time for UV radiation exposure of the area based on the UV radiation exposure data.

In some embodiments, the processor is further configured to activate an alarm in response to the current UV radiation exposure value exceeding the threshold UV radiation exposure value. In some embodiments, the processor is configured to generate a questionnaire for the user regarding the at least one physical characteristic. In these and other embodiments, the input includes input from the user in response to the questionnaire. In some embodiments, the input includes an image of the at least one physical characteristic.

In some embodiments, the wearable UV light sensor assembly includes an adaptable housing configured for use in at least one of the areas of the user's body. In some embodiments, the wearable UV light sensor assembly is configured to selectively transmit the current ultraviolet (UV) radiation level and the exposure time to the processor. In some embodiments, the wearable UV light sensor assembly is configured to selectively transmit the current ultraviolet (UV) radiation level and the exposure time to the processor at periodic intervals. In certain embodiments, the system includes a notification system configured to provide to the user an auditory alarm, haptic feedback, and/or a visual notification.

According to another aspect of the present disclosure, the method for monitoring UV radiation exposure and notifying a user of a risk of overexposure includes receiving, by a processor, input including at least one physical characteristic of a user. The method further includes receiving, by the processor, body mapping data for the user and assessing, by the processor, a UV exposure risk for each of multiple areas of the user's body based on the input and the body mapping data.

The method includes determining, based on the UV exposure risk, a threshold UV radiation exposure value for each of the areas. A wearable ultraviolet (UV) light sensor is configured to be worn by the user in at least one of the areas and is used to detect a current UV radiation level and an exposure time. The exposure time indicates an amount of time that the area has been exposed to UV radiation. The method further includes determining, by the processor, a current UV radiation exposure value for the area based on the current UV radiation level and the exposure time. The processor compares the current UV radiation exposure value to the threshold UV radiation exposure value for the area to generate UV radiation exposure data. The processor notifies the user of a remaining time for UV radiation exposure based on the UV radiation exposure data.

In some embodiments, the method further includes activating, by the processor, an alarm in the event the current UV radiation exposure value exceeds the threshold UV radiation exposure value. In some embodiments, the method further includes generating, by the processor, a questionnaire for the user regarding the at least one physical characteristic. In some embodiments, receiving the input includes receiving input from the user in response to the questionnaire.

In some embodiments, the input includes an image of the at least one physical characteristic. The method further includes analyzing, by the processor, the image to determine a skin type of the user. In some embodiments, determining the current UV radiation level comprises detecting a UV-A radiation level and a UV-B radiation level and weighing the UV-B radiation level more heavily than the UV-A radiation level.

In some embodiments, detecting the current UV radiation level comprises detecting the current UV radiation level at periodic intervals. In some embodiments, the method includes aggregating the UV radiation exposure data for the user over a predetermined period of time and generating a customized report for the user based thereon. The customized report may include at least one recommendation for protection from UV radiation exposure.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Figure 1:
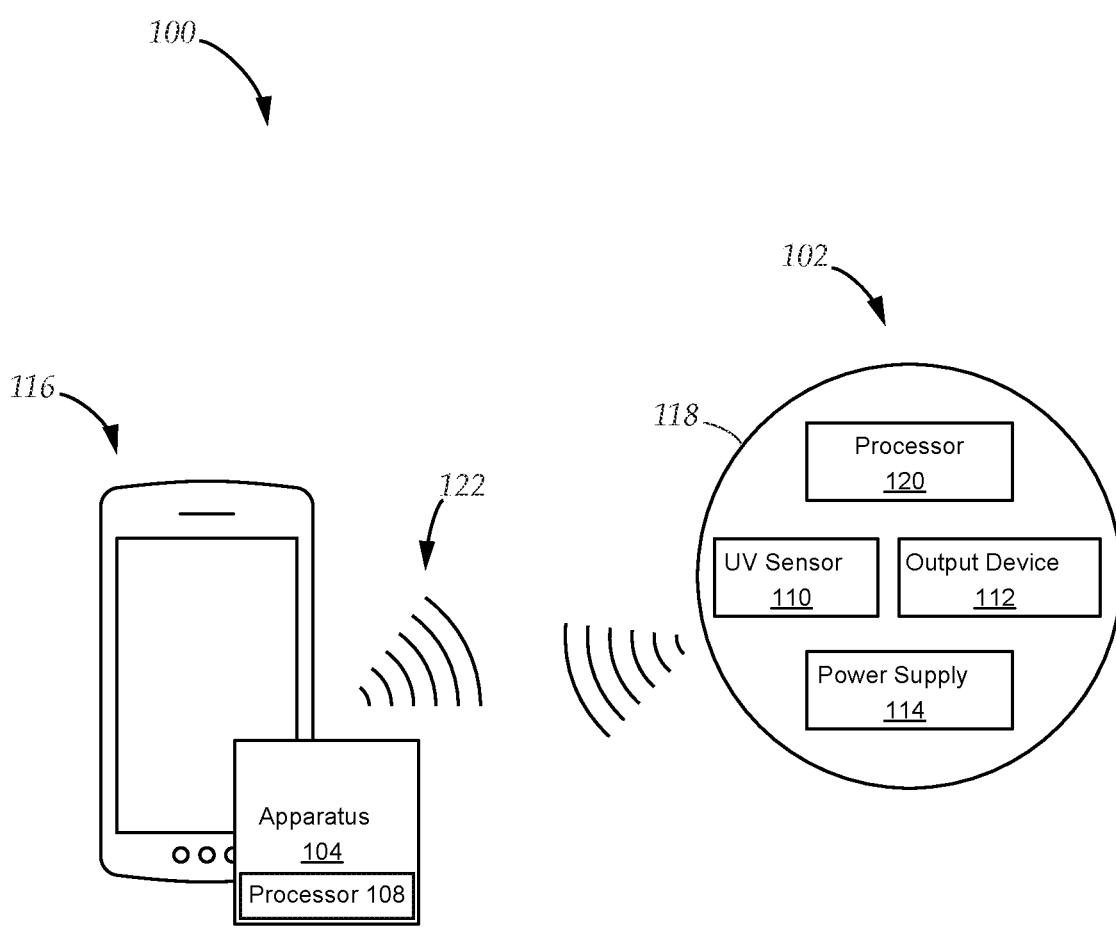
FIG. 1 is a schematic plan diagram illustrating one embodiment of a UV radiation exposure notification system including a wearable UV light sensor assembly and a computing device in accordance with some embodiments of the disclosure.

As previously discussed, it is essential for individuals to be aware of their UV radiation exposure levels and to take appropriate measures to mitigate risks. Existing methods for monitoring UV radiation exposure tend to rely on subjective assessments or intermittent measurements using standalone devices. These devices and methods may not provide real-time feedback or personalized recommendations based on individual characteristics and environmental conditions. The present disclosure addresses these and other issues.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise.

The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Furthermore, the described features, structures, or characteristics of the invention may be combined in any suitable manner in one or more embodiments. In the following description, numerous specific details are provided, such as examples of programming, software modules, user selections, network transactions, database queries, database structures, hardware modules, hardware circuits, hardware chips, etc., to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments.

These features and advantages of the embodiments will become more fully apparent from the following description and appended claims or may be learned by the practice of embodiments as set forth hereinafter. As will be appreciated by one skilled in the art, aspects of the present invention may be embodied as a system, method, and/or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, aspects of the present invention may take the form of a computer program product embodied in one or more computer readable medium(s) having program code embodied thereon.

Many of the functional units described in this specification have been labeled as modules, in order to more particularly emphasize their implementation independence. For example, a module may be implemented as a hardware circuit comprising custom very large scale integrated ("VLSI") circuits or gate arrays, off-the-shelf semiconductors such as logic chips, transistors, or other discrete components. A module may also be implemented in programmable hardware devices such as a field programmable gate array ("FPGA"), programmable array logic, programmable logic devices or the like.

Modules may also be implemented in software for execution by various types of processors. An identified module of program code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of program code may be a single instruction, or many instructions, and may even be distributed over several different code segments, among different programs, and across several memory devices. Similarly, operational data may be identified and illustrated herein within modules and may be embodied in any suitable form and organized within any suitable type of data structure. The operational data may be collected as a single data set or may be distributed over different locations including over different storage devices, and may exist, at least partially, merely as electronic signals on a system or network. Where a module or portions of a module are implemented in software, the program code may be stored and/or propagated on in one or more computer readable medium(s).

The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory ("RAM"), a read-only memory ("ROM"), an erasable programmable read-only memory ("EPROM" or Flash memory), a static random access memory ("SRAM"), a portable compact disc read-only memory ("CD-ROM"), a digital versatile disk ("DVD"), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture ("ISA") instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network ("LAN") or a wide area network ("WAN"), or the connection may be made to an external computer (for example, through the Internet using an Internet Service Provider). In some embodiments, electronic circuitry including, for example, programmable logic circuitry, field-programmable gate arrays ("FPGA"), or programmable logic arrays ("PLA") may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of program instructions may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

The schematic flowchart diagrams and/or schematic block diagrams in the Figures illustrate the architecture, functionality, and operation of possible implementations of apparatuses, systems, methods and computer program products according to various embodiments of the present invention. In this regard, each block in the schematic flowchart diagrams and/or schematic block diagrams may represent a module, segment, or portion of code, which comprises one or more executable instructions of the program code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

As used herein, a list with a conjunction of "and/or" includes any single item in the list or a combination of items in the list. For example, a list of A, B and/or C includes only A, only B, only C, a combination of A and B, a combination of B and C, a combination of A and C or a combination of A, B and C. As used herein, a list using the terminology "one or more of" includes any single item in the list or a combination of items in the list. For example, one or more of A, B and C includes only A, only B, only C, a combination of A and B, a combination of B and C, a combination of A and C or a combination of A, B and C. As used herein, a list using the terminology "one of" includes one and only one of any single item in the list. For example, "one of A, B and C" includes only A, only B or only C and excludes combinations of A, B and C. As used herein, "a member selected from the group consisting of A, B, and C," includes one and only one of A, B, or C, and excludes combinations of A, B, and C. As used herein, "a member selected from the group consisting of A, B, and C and combinations thereof" includes only A, only B, only C, a combination of A and B, a combination of B and C, a combination of A and C or a combination of A, B and C.

Figure 2:
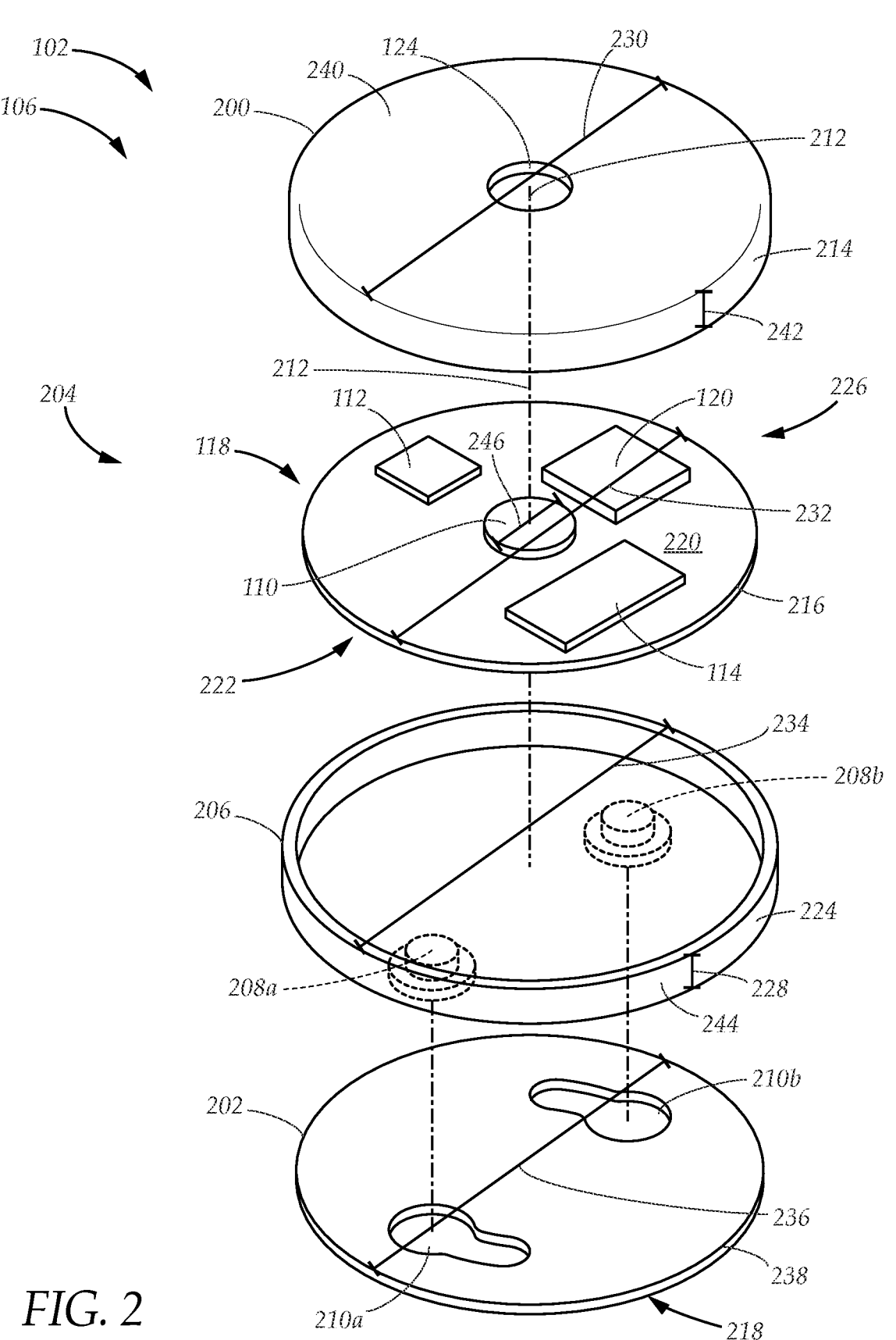
FIG. 2 is an exploded perspective view of one embodiment of wearable UV light sensor assembly including a processor, a UV sensor, a power supply, and a communication device contained within a housing assembly in accordance with certain embodiments of the disclosure.

Referring now to FIGS. 1 and 2, a system 100 for monitoring UV radiation exposure and notifying a user of a risk of overexposure is illustrated. In some embodiments, the system 100 includes a wearable ultraviolet (UV) light sensor assembly 102 in electronic communication with a computing device 116. The computing device 116 includes a UV radiation exposure monitoring apparatus 104 configured to assess a user's UV radiation exposure and to notify the user of potential overexposure based on the assessment. The UV light sensor assembly 102 and the computing device 116 may work together to assist a user in understanding their exposure to UV radiation and may facilitate prevention of skin damage due to overexposure.

In some embodiments, as discussed in more detail below, the wearable UV light sensor assembly 102 is configured to receive input and to selectively transmit information, such as a current UV radiation level and exposure time, to a computing device 116. The computing device 116 may include a UV radiation exposure monitoring apparatus 104 and a processor 108. In some embodiments, the computing device 116 is a remote computing device 116 configured to communicate with the UV light sensor assembly 102 via a wireless connection 102.

In some embodiments, the UV light sensor assembly 102 is further configured to store and/or process at least a portion of the information. In some embodiments, the wearable UV light sensor assembly 102 is configured to selectively transmit at least a portion of the information, such as the current UV radiation level and the exposure time, to the processor 108. In some embodiments, the UV light sensor assembly 102 is configured to transmit the information to the processor 108 continuously, intermittently, periodically, upon request from the processor 108, and/or at any other desired time. In some examples, selectively transmitting the current UV radiation level includes transmitting only UV radiation measurements that fall within a predetermined range of wavelengths and/or wavelengths within a predetermined range of intensities.

In some embodiments, the UV light sensor assembly 102 is configured to operate in temperatures ranging between about −30 to about 80° C., thereby facilitating user participation in a wide variety of outdoor activities including, for example, hiking and biking in desert-like climates and participating in cold-weather sports like skiing or snowmobiling. In some embodiments, the UV light sensor assembly 102 is water-resistant and/or incorporates materials configured to protect the device from water damage, thereby facilitating use of the UV light sensor assembly 102 in connection with activities in inclement weather such as rain or snow, and/or activities that involve water, such as kayaking or paddleboarding.

Figure 8:
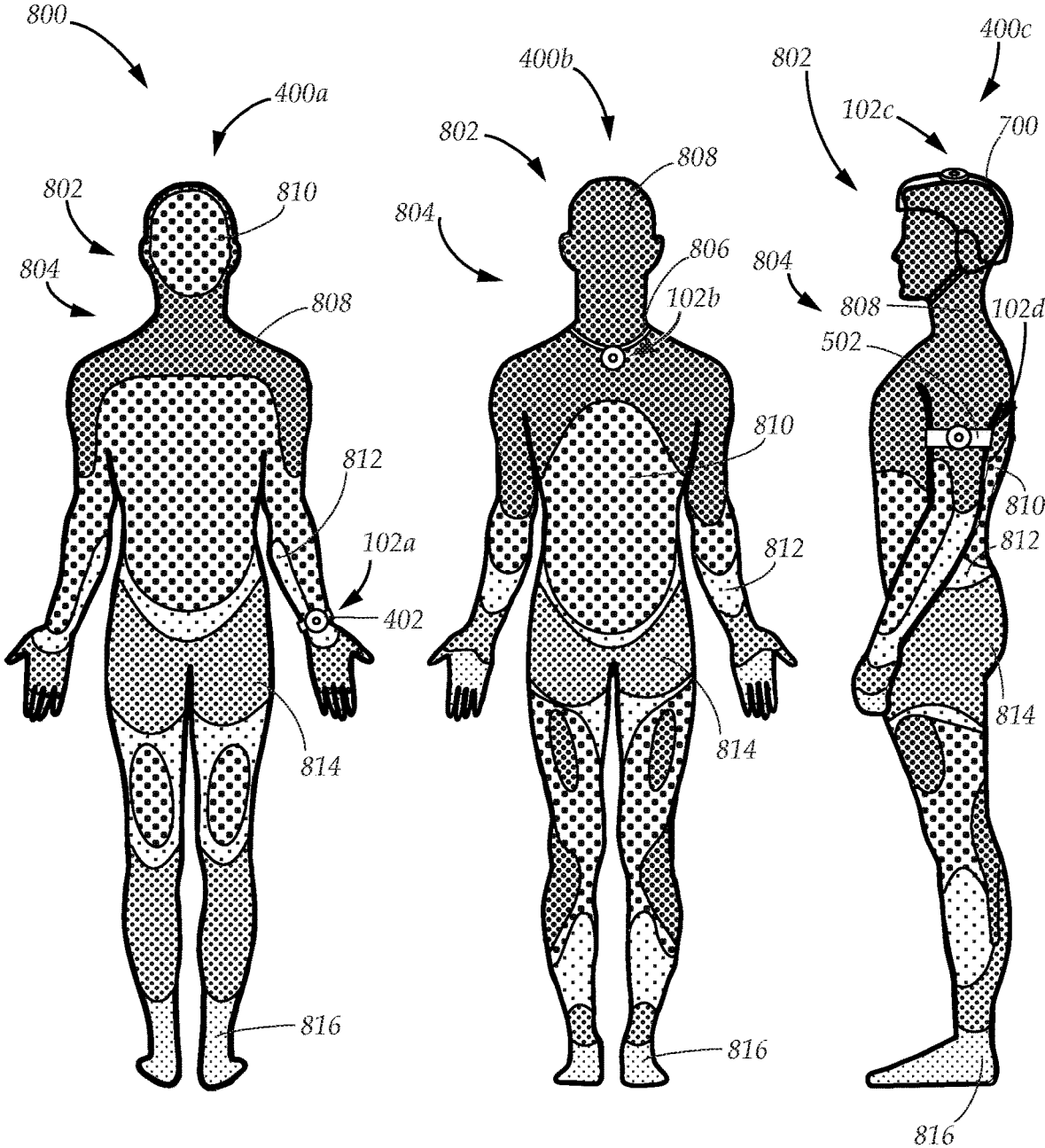
FIG. 8 is a schematic plan diagram illustrating body mapping data for positioning a wearable UV light sensor assembly to correspond to any of various areas of a user's body in accordance with some embodiments of the disclosure.

In some embodiments, as shown in FIG. 8, while still referring to FIGS. 1 and 2, the UV light sensor assembly 102 is configured to detect a current UV radiation level corresponding to a specified region or area 804 of the user's body. In some embodiments, the UV light sensor assembly 102 is adaptable, movable, and/or modifiable such that the UV light sensor assembly 102 may be strategically placed in or attached to any of multiple regions or areas 804 of the user's body to detect a UV radiation level corresponding to that area 804.

In certain embodiments, the UV light sensor assembly 102 is configured to detect and/or record a UV exposure time corresponding to a region or area of the user's body at which the UV light sensor assembly 102 is placed or attached. In other words, in some embodiments, the UV light sensor assembly 102 is configured to be worn by the user such that the UV light sensor assembly 102 corresponds to at least one of multiple areas of the user's body, and the UV light sensor assembly 102 is configured to detect and/or record the amount of time that the area has been exposed to UV radiation.

Figure 3:
FIG. 3 is a perspective view of the wearable UV light sensor assembly of FIG. 2 assembled in accordance with some embodiments of the disclosure.
Figure 3:
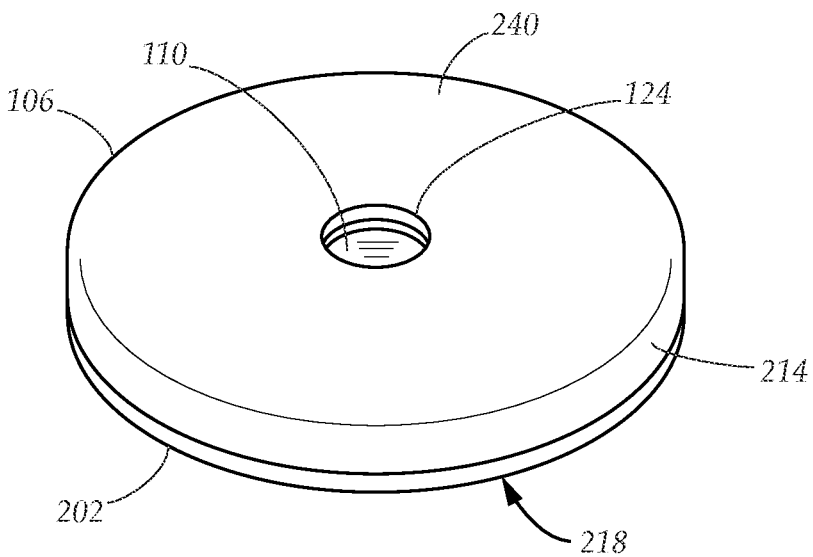

Referring now to FIGS. 2 and 3, while also referring to FIG. 1, in some embodiments, the UV light sensor assembly 102 includes one or more component parts 204 including, for example, a printed circuit board 118, a housing lid 200, a housing base 202, and a housing case 206. In some embodiments, the housing base 202 is omitted. In some embodiments, each of the component parts 204 is aligned along a central axis 212. The printed circuit board 118 may be substantially planar and may include an upper surface 220 and a lower surface 222. In some embodiments, the printed circuit board 118 includes a round or substantially circular shape. In other embodiments, the printed circuit board 118 includes any suitable size and/or shape.

In one embodiment, the printed circuit board 118 is a round circuit board having a diameter of about fifty (50 mm) millimeters or less. In certain embodiments, the printed circuit board 118 includes a thickness between about one and about two millimeters (1-2 mm). In one embodiment, the printed circuit board 118 includes a thickness of 1.6 millimeters (1.6 mm). In some embodiments, the printed circuit board 118 includes a double-layer printed circuit board including about one ounce (1 oz) or less of finishing copper. Of course, the printed circuit board 118 may include any suitable materials and/or dimensions. In some embodiments, the printed circuit board 118 may include one or more materials selected to withstand a specific climate or condition, such as warm and/or wet environments.

In some embodiments, the printed circuit board 118 is coupled to various hardware elements 226 via through-hole mounting, surface mount technology, ball grid array, pin grid array, flip-chip technology, wire bonding, a press fit, an adhesive, and/or the like. In these and other embodiments, one or more of the hardware elements 226 may be coupled to the upper surface 220 and/or the lower surface 222 of the printed circuit board 118. In some embodiments, one or more of the hardware elements 226 extends through the printed circuit board 118 between the upper surface 220 and the lower surface 222.

In some embodiments, the hardware elements 226 include a processor 120, a communication device 112, and/or a power supply 114. In some embodiments, the processor 120 includes a microcontroller, a signal processor a field-pro-grammable gate array (FPGA), or the like. In one embodi-ment, the processor 120 includes an embedded processing system such as Raspberry Pi.

In some embodiments, the UV light sensor assembly 102 includes a communication device 112 such as a Bluetooth® chip or other suitable wireless communication device con-figured to communicate with the processor 108 of the computing device 116. In some embodiments, the commu-nication device 112 is configured to communicate with the computing device 116 via any wireless or near-field com-munication method known to those in the art, such as Wi-Fi, radio frequency identification (RFID), infrared (IR), Blu-etooth®, and/or the like. In some embodiments, the com-puting device 116 may include a mobile computing device such as a mobile phone, a laptop computing device, a tablet computing device, or the like. In these and other embodi-ments, a user may carry the computing device 116 on or near his person to facilitate communication with the UV light sensor assembly 102 via the communication device 112.

In some embodiments, the power supply 114 includes a lithium-ion battery or other suitable low-energy power sup-ply 114. In one embodiment, the power supply 114 includes a 3.6 V lithium-ion coin cell battery.

In some embodiments, the UV sensor 110 includes a round UV sensor 110 having a diameter 246 less than the diameter 232 of the printed circuit board 118. The UV sensor 110 may be attached to the printed circuit board 118 by any suitable fastening device or technique. In some embodi-ments, the UV sensor 110 is substantially centered with respect to the printed circuit board 118 and/or the central axis 212. In these and other embodiments, the UV sensor 110 may be exposed through an aperture 124 disposed through the housing lid 200. In some embodiments, the UV sensor 110 and the aperture 124 include substantially con-gruent shapes. In other embodiments, the UV sensor 110 includes dimensions at least slightly less than the aperture 124 to maximize exposure of the UV sensor 110 to UV radiation through the aperture 124.

In some embodiments, the UV light sensor 110 is con-figured to identify UV light within the UV-A and the UV-B spectrums. In certain embodiments the UV sensor 110 is configured to identify UV light having a wavelength between about two hundred eighty nanometers (280 nm) and about four hundred nanometers (400 nm). In some examples, the UV light sensor 110 includes a narrowband UV sensor configured to detect UV radiation within a specific wavelength range. In some examples, the UV light sensor 110 is configured to differentiate between UV-A and UV-B radiation. In some examples, the UV light sensor 110 includes at least one of a photodiode UV sensor, a photo-multiplier tube (PMT) UV sensor, and/or any combination thereof. In some examples, the UV light sensor 110 is a broadband UV sensor.

In some embodiments, the printed circuit board 118 and its various hardware elements 226 are encased within a housing assembly 106. The housing assembly 106 may include any suitable size and/or shape and may be assembled such that each of the component parts 204 aligns along a central axis 212. In some embodiments, one or more of the component parts 204 includes complementary features con-figured to selectively engage one another to hold the housing assembly 106 together and/or to provide structural support to the housing assembly 106. In some embodiments, for example, one or more of the component parts 204 includes threads, grooves, and/or pronged elements configured to fit, twist, and/or otherwise lock into place when engaged with a corresponding feature of another component part 204. In one embodiment, at least one component parts 204 of the hous-ing assembly 106 includes a three-pronged part configured to be inserted into a corresponding space in another com-ponent part 204 to provide twist-lock capabilities.

In certain embodiments, one or more attachment elements 208*a*, 208*b* may be configured to extend through more than of the component parts 204 to hold the housing assembly 106 together and/or to provide structural support. In some embodiments, an attachment element 208*a*, 208*b* includes, for example, a pole, a screw, a bolt, a rivet, a grommet, a clip, an adhesive, and/or any other suitable mechanical feature or device known to those in the art. In certain embodiments, the housing assembly 106 is monolithically formed as a single unit.

In some embodiments, the housing assembly 106 includes a housing case 206, a housing lid 200, and/or a housing base 202. In certain embodiments, the housing case 206 is disposed between the housing lid 200 and the housing base 202. In some embodiments, the housing assembly 106 includes a substantially rigid or semi-rigid material config-ured to withstand UV radiation and mechanical stresses. In some embodiments, for example, the housing assembly 106 includes a suitable thermoplastic material such as acryloni-trile butadiene styrene (ABS) and/or polycarbonate (PC). In other embodiments, the housing assembly 106 includes one or more suitable synthetic materials such as polyethylene (PE), polypropylene (PP), acrylic (PMMA), polyethylene terephthalate (PET), polyoxymethylene (POM), and/or the like.

In some embodiments, the housing case 206 includes a shape and/or dimensions such that the housing case 206 substantially surrounds the printed circuit board 118 and its associated hardware elements 226. In some embodiments, the housing case 206 is coupled to or integrated with the housing base 202. In some embodiments, the housing base 202 includes a size and shape substantially identical to the size and shape of the printed circuit board 118 such that the printed circuit board 118 is disposed directly on top of and aligned with the housing base 202 within the housing assembly 106. In some embodiments, one or more attach-ment elements 208*a*, 208*b* is configured to couple one or more of the component parts 204 together when the UV light sensor assembly 102 is assembled.

In some embodiments, the housing case 206 is defined by a wall 224 extending substantially parallel to the central axis 212. The housing case 206 may be coupled to the housing base 202 such that the wall 224 extends substantially per-pendicularly from an outside edge 238 of the housing base 202. In one embodiment, the wall 224 defines a circular shape having a diameter 234 at least slightly greater than a diameter 232 of the printed circuit board 118. In this manner, the wall 224 may be disposed adjacent to and may substan-tially circumscribe a periphery 216 of the printed circuit board 118. In some embodiments, a height 228 of the wall 224 defines a depth of the housing assembly 106.

In some embodiments, the housing case 206, the housing lid 200 and the housing case 206 include substantially congruent shapes. In some embodiments, the housing lid

200 includes a top surface diameter 230 at least slightly greater than the diameters 232, 234, 236 of the printed circuit board 118, the housing case 206, and housing base 202. In some embodiments, the housing lid 200 includes a lip 214 extending substantially perpendicularly from the top surface 240 of the housing lid 200. In some embodiments, the lip 214 is configured to extend at least partially over and adjacent to an outer surface 244 of the wall 224 of the housing case 206 to encase the printed circuit board 118 within the housing assembly 106. In some embodiments, the lip 214 includes a height 242 substantially identical to or greater than a height 228 of the wall 224.

In some embodiments, the housing lid 200 includes a cutout or aperture 124 substantially corresponding the size, shape, and/or position of the UV sensor 110 on the printed circuit board 118. In these and other embodiments, at least a portion of the UV sensor 110 may be directly exposed to UV radiation through the housing lid 200 when the housing assembly 106 is fully assembled.

Referring now to FIGS. 4, 5A, 5B, 6, and 7, in some embodiments, the housing base 202 and/or another component parts 204 or portions of the housing assembly 106 includes one or more features or attachment points configured to secure or couple an accessory or attachment device to the UV light sensor assembly 102. In some embodiments, for example, an accessory or attachment device includes an armband, a wristband, a headband, a loop, a clip, a helmet, a necklace, a lanyard, a combination thereof, and/or the like. In some embodiments, as shown in FIG. 2, the housing base 202 and/or other component part 204 includes one or more apertures 210a, 210b configured to receive at least a portion of strap of the accessory or attachment device therethrough.

Figure 4:
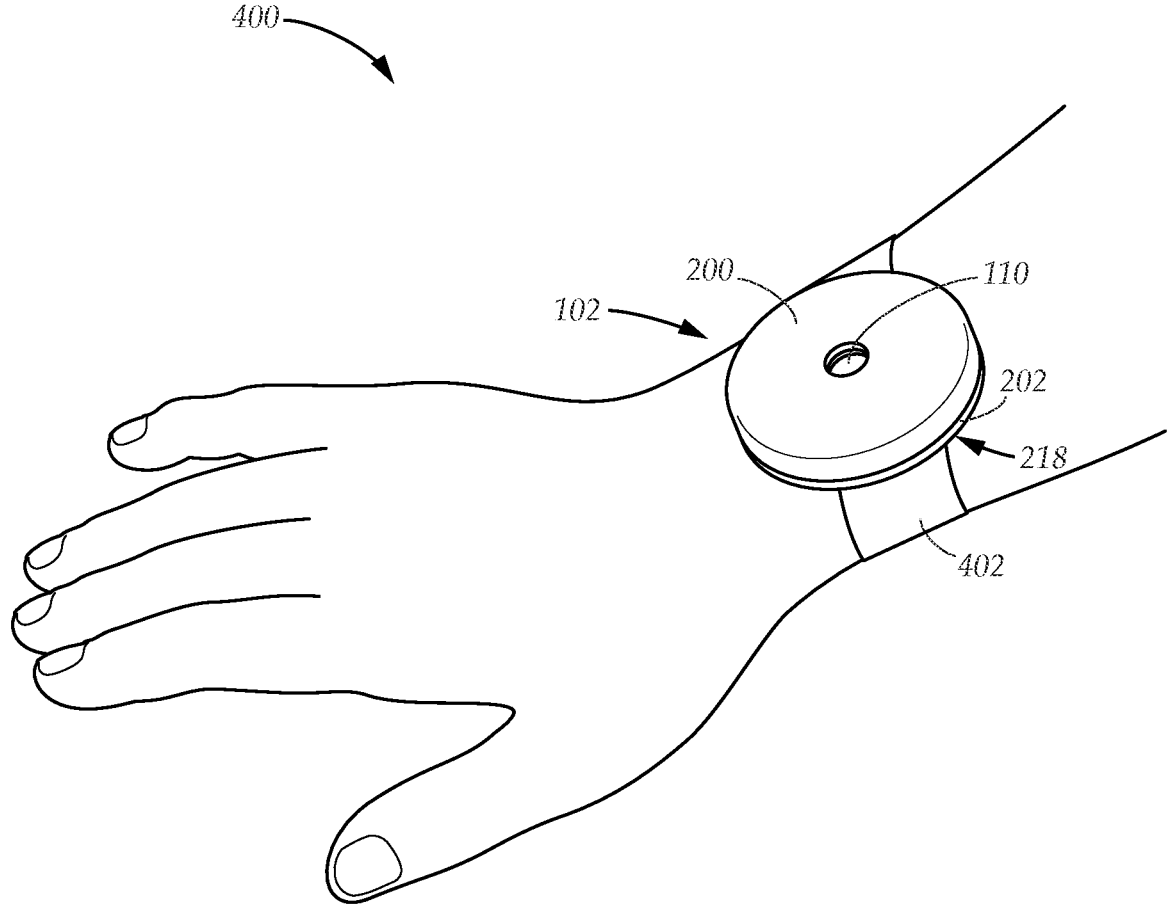
FIG. 4 is a perspective view of one embodiment of the wearable UV light sensor assembly that includes a wristband configured to be worn by a user in accordance with some embodiments of the disclosure.

As illustrated in FIG. 4, while also referring to FIG. 2, in some embodiments, the UV light sensor assembly 102 is attached to a user 400 via a wristband 402. In some embodiments, a length of the wristband 402 extends through the apertures 210a, 210b to integrate the UV light sensor assembly 102 with the wristband 402. In some embodiments, the wristband 402 may include a substantially flexible, wear-resistant material such as silicone, nylon, polyester, leather, rubber, vinyl, fabric, and/or any other suitable material. In some embodiments, the wristband 402 includes an elastic material. In certain embodiments, the wristband 402 is substantially planar and includes dimensions configured to comfortably fit various users.

Figure 5A:
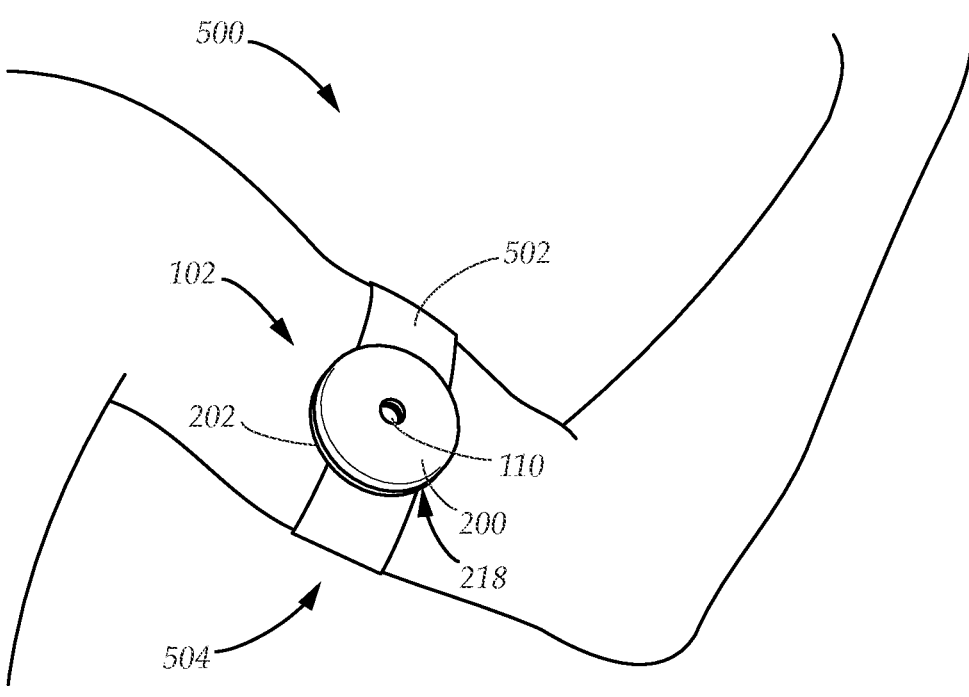
FIG. 5A is a perspective view of another embodiment of the wearable UV light sensor assembly that includes an armband configured to be worn by a user in accordance with some embodiments of the disclosure.
Figure 5B:
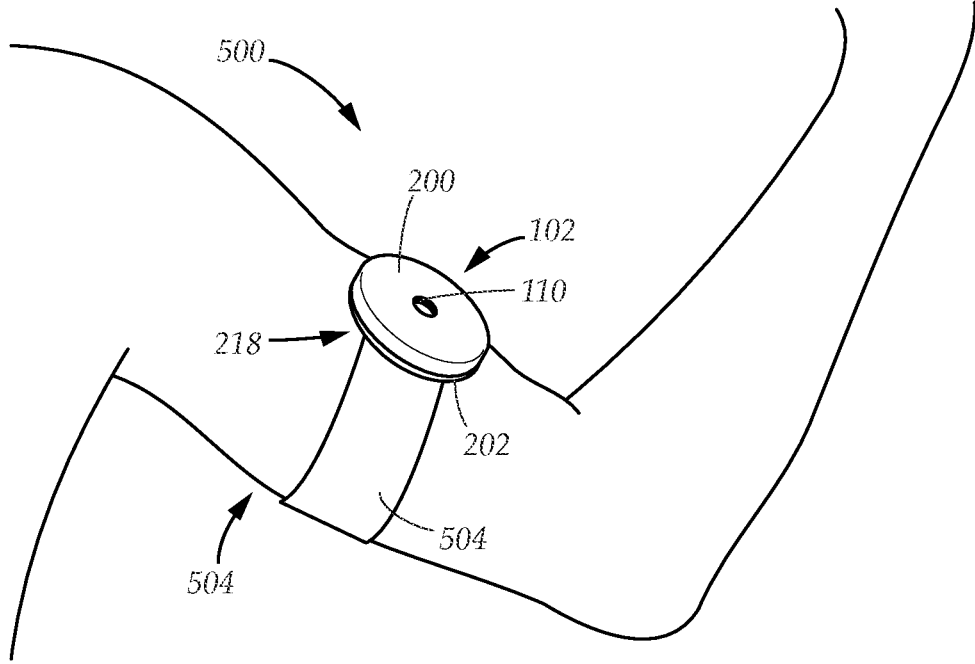
FIG. 5B is a perspective view of the wearable UV light sensor assembly of FIG. 5A rotated to another position on the user's arm in accordance with some embodiments of the disclosure.

Similarly, in some embodiments as shown in FIGS. 5A and 5B, while also referring to FIG. 2, the UV light sensor assembly 102 is attached to a user 500 via an armband 502. In some embodiments, a length of the armband 502 extends through the apertures 210a, 210b to integrate the UV light sensor assembly 102 with the armband 502. In some embodiments, the armband 502 may include a substantially flexible, wear-resistant material such as silicone, nylon, polyester, leather, rubber, vinyl, fabric, and/or any other suitable material. In some embodiments, the armband 502 includes an elastic material and/or may be adjusted via a suitable mechanical feature or device such as a hook and loop fabric or the like. In some embodiments, the UV light sensor assembly 102 is rotatable with respect to the armband 502. In these and other embodiments, the UV light sensor assembly 102 may be selectively rotated to ensure that the UV sensor 110 is exposed to direct sunlight and/or to maintain comfort. In certain embodiments, the armband 502 is substantially planar and includes dimensions configured to comfortably fit various users.

Figure 6:
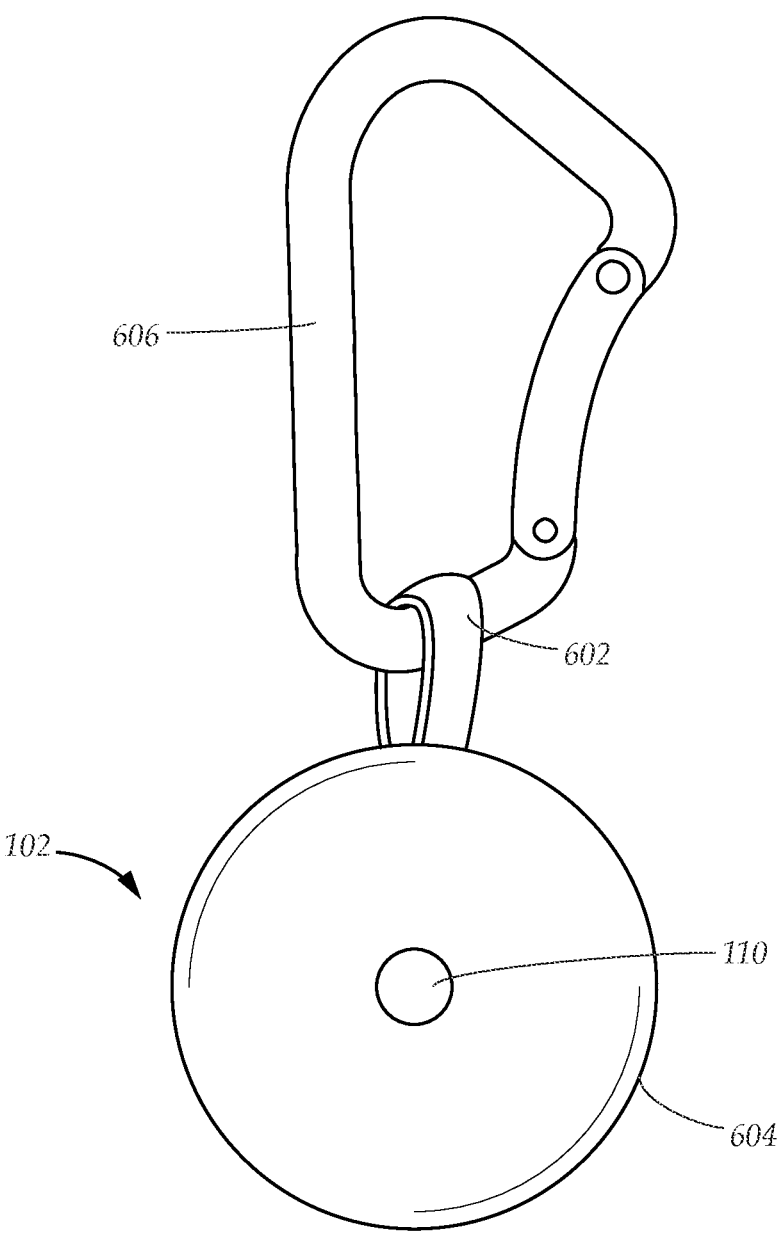
FIG. 6 is a front view of another embodiment of the wearable UV light sensor assembly that includes an attachment element configured to be attached to an item in accordance with some embodiments of the disclosure.

Referring now to FIG. 6, in some embodiments, the UV light sensor assembly 102 is configure to attach to a cara-biner or other suitable clip or attachment device 606. In these and other embodiments, the UV light sensor assembly 102 may be attached to a variety of secure locations on the body, garments, or accessories. In some embodiments, the housing base 202 or other component part 204 of the housing assembly 106 is securely coupled to a looped attachment point 602 via one or more suitable mechanical fasteners such as a bolt, a rivet, a grommet, an adhesive, and/or the like. In some embodiments, at least a portion of the looped attachment point 602 is configured to extend laterally beyond a perimeter 604 of the UV light sensor assembly 102. In some embodiments, the attachment device 606 is configured to be coupled to the UV light sensor assembly 102 by threading the attachment device 606 through the looped attachment point 602. In this manner, the attachment device 606 may couple the UV light sensor assembly 102 to any of various garments, items, or accessories as desired. In other embodiments, any suitable accessory may be threaded through the looped attachment point 602 to facilitate attaching the UV light sensor assembly 102 to a desired item. For example, the accessory may include a necklace, a lanyard, a strap, or any other suitable item.

Figure 7:
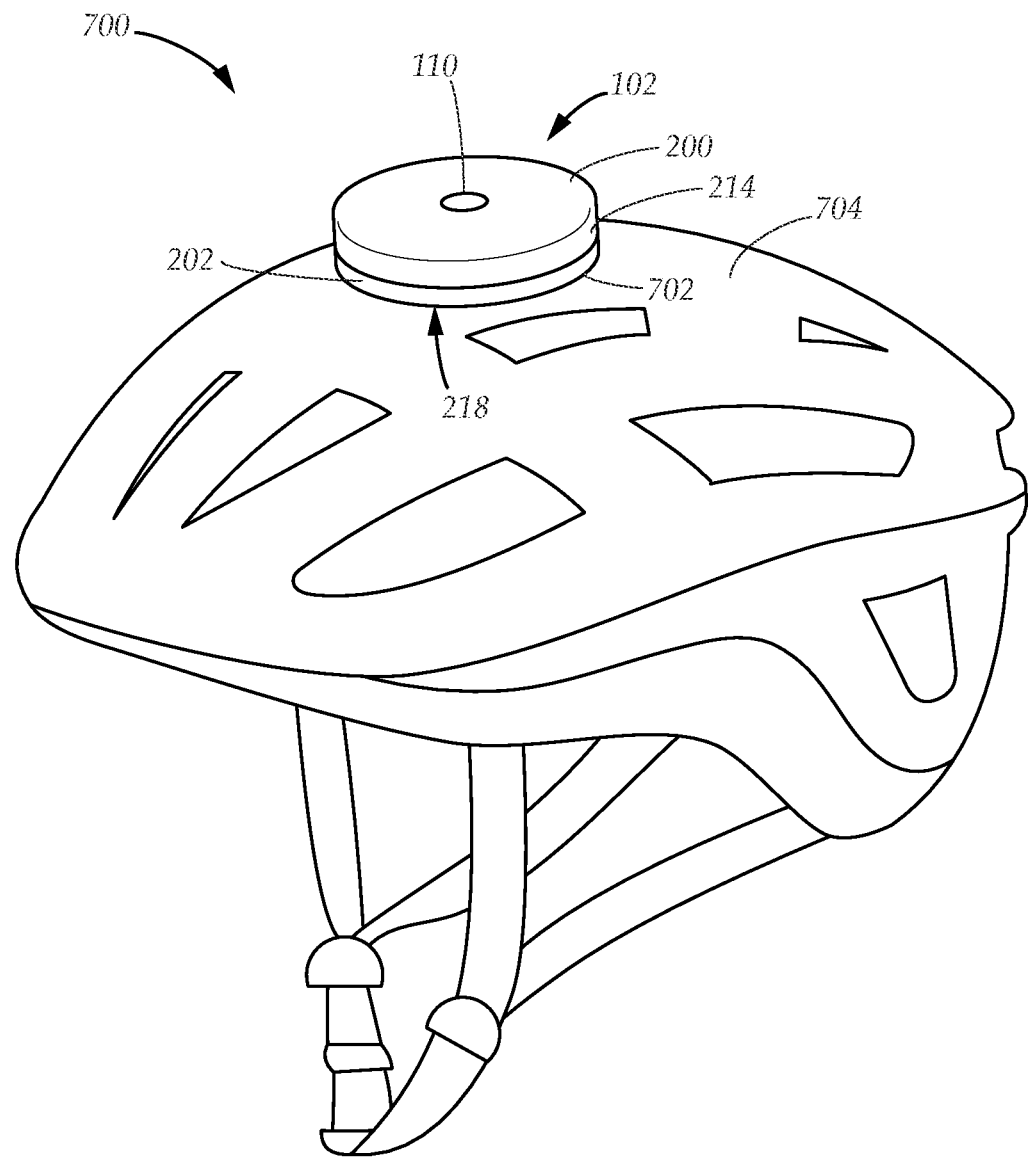
FIG. 7 is a perspective view of one embodiment of the wearable UV light sensor assembly that includes an attachment element configured to be attached to the top of a helmet in accordance with some embodiments of the disclosure.

Referring now to FIG. 7, in some embodiments, the UV light sensor assembly 102 is mounted to a helmet 700 via a rigid mounting element 702 coupled to or integrated with a portion of the helmet 700. In one embodiment, the mounting element 702 is mounted to a top surface 704 of the helmet 700. In some embodiments, the mounting element 702 is removably or fixably coupled to the housing base 202 or other portion of the housing assembly 106 to mount the UV light sensor assembly 102 to the helmet 700. In some embodiments, the mounting element 702 includes a curvature substantially corresponding to a curvature of the top surface 704 of the helmet 700. In this manner, the UV light sensor assembly 102 may be securely maintained against the top surface 704 of the helmet 700 for secure and reliable use during various activities including, for example skiing, biking, snowmobiling, and the like.

Referring now to FIG. 8, while also referring to FIG. 1, in some embodiments, the UV light sensor assembly 102 is versatile and may be used in any of multiple regions or areas 804 of a user's 400a, 400b, 400c body 802. In some embodiments, UV light sensor assembly 102 is configured to be attached to various items or accessories to facilitate positioning the UV light sensor assembly 102 to correspond to a desired area 804. As discussed above, such items or accessories may include a wristband 402, an armband 502, a helmet 700, a necklace, a lanyard, a strap, a headband, a leg band, an ankle band, or any other suitable item or accessory.

In some embodiments, the user 400a, 400b, 400c selectively wears, places, or otherwise positions a UV light sensor assembly 102 to correspond to an area 804 that is known to be particularly susceptible or prone to UV radiation exposure. In some embodiments, body mapping data 800 may be utilized to facilitate selection of such an area 804.

In some embodiments, body mapping data 800 for the user 400a, 400b, 400c is generated by the processor 108 of the computing device 116. In some embodiments, the body mapping data 800 is based on generalized data as well as on input from the user 400a, 400b, 400c. In some embodiments, the body mapping data 800 is used to assess a UV exposure risk corresponding to each of the areas 804. In some embodiments, the body mapping data 800 divides the body 802 into various areas 804 and indicates the relative susceptibility of each of the areas 804 to skin cancer and/or other damage from UV exposure. In some embodiments, the body mapping data 800 is customized to a user 400a, 400b, 400c based at least partially on input received from the user 400a, 400b, 400c.

As shown, in some embodiments, the body mapping data 800 may include a visual representation of relative susceptibility of various areas 804 of the user 400a, 400b, 400c to skin cancer and/or other damage caused by UV radiation exposure. For example, a first region 808 may have the highest susceptibility to damage from UV radiation expo- sure, while other areas 804 may indicate decreased relative susceptibility from a second region 810 to a third region 812 to a fourth region 814 and finally to a fifth region 816.

In one embodiment, the user 400a utilizes a wristband 402 to position the UV light sensor assembly 102a within the second region 810. In another embodiment, the user 400b utilizes a necklace 806 to position the UV light sensor assembly 102b within the first region 808. In another embodiment, the user 400c places more than one UV light sensor assembly 102c, 102d to correspond to more than one area 804 within the first region 808. For example, as shown, the user 400c may utilize an armband 502 to position a first UV light sensor assembly 102 in one area 804 of the first region 808 and may utilize a helmet 700 to position a second UV light sensor assembly 102 in another area 804 within the first region 808.

In some examples, the monitoring apparatus 104 is con- figured to scan the user 400's body and to present the user 400 with body mapping data 800 customized to the user's 400 body 802. In some examples, the body mapping data 800 is generated without scanning or taking a photo of the user 400 and is instead a generalized representation of the human body 802. In some examples, the monitoring appa- ratus 104 is configured to receive input from the user 400 regarding particular areas 804 of concern on their body 802. For example, the user 400 can select certain areas 804 of concern via the computing device 116. In some examples, in response to determining that the user 400 has selected an area 804 of concern, the monitoring apparatus 104 is con- figured to prompt the user 400 400 to upload images of that area 804.

Figure 9:
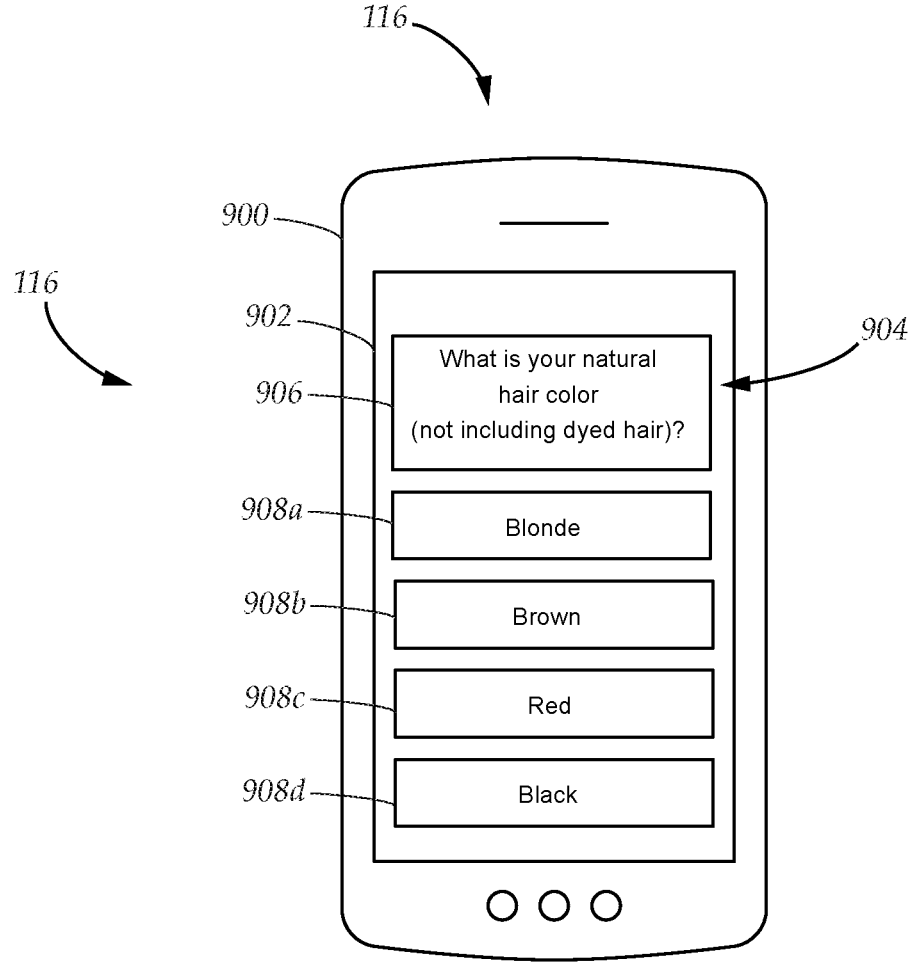
FIG. 9 is a front view of a representative computing device including one embodiment of an apparatus configured to display a query regarding a physical characteristic of a user and various selectable input options in response to the query in accordance with some embodiments of the disclosure.

Referring now to FIG. 9, while also referring to FIG. 1, the system 100 includes a computing device 116, such as a laptop computing device, a mobile phone, a tablet comput- ing device, or other suitable computing device 116, in communication with the wearable UV light sensor assembly 102 via a wired or wireless connection 122. In some embodiments, the computing device 116 includes a UV radiation exposure monitoring apparatus 104 and a user input device 902. The UV radiation exposure monitoring apparatus 104 may include one or more processors 108 and non-transitory computer-readable storage media storing code executable by the processors 108 to perform opera- tions. The UV radiation exposure monitoring apparatus 104 may be configured to receive user 400 input 908a-908d via the user input device 902. The user input device 902 may include, for example, a touchscreen, a keyboard, a stylus, and/or the like.

In some embodiments, the UV radiation exposure moni- toring apparatus 104 is configured to enable the user 400 to initialize a Wi-Fi or other wireless connection 122 between the computing device 116 and a local wireless network. In some embodiments, the UV radiation exposure monitoring apparatus 104 running on the computing device 116 allows the user 400 to initialize and/or customize the UV light sensor assembly 102 according to their preferences. The wireless connection 122 may also allow the UV light sensor assembly 102 to stream data to a remote server (not shown) either via the computing device 116 or directly through the wireless connection 122.

In some embodiments, the UV radiation exposure moni- toring apparatus 104 is configured to receive physical char- acteristic input 908a-908d regarding at least one physical characteristic of the user 400. In some embodiments, the UV radiation exposure monitoring apparatus 104 generates a questionnaire 904 that includes one or more queries 902 regarding at least one physical characteristic of the user 400. The UV radiation exposure monitoring apparatus 104 may be further configured to display the questionnaire 904 to the user 400 via a display element 900. In some embodiments, the display element 900 includes a display element 900 of a computing device 116, such as a phone, tablet, computer, etc. In some examples, a user interface (e.g., a graphical user interface) is displayed on the display element 900.

In some embodiments, the questionnaire 904 includes one or more queries 906 regarding the user's 400 genetic con- ditions and/or sun exposure habits. In some examples, the queries 906 are regarding the user 400's natural hair color, eye color, skin color, skin sensitivity, and/or the like. In some examples, the queries include questions related to the user's predisposition to conditions such as erythemal red- dening, sun damage, and/or skin cancer. In some examples, a quantity of the queries 906 is not less than five (5) and not greater than twenty (20).

Figure 11:
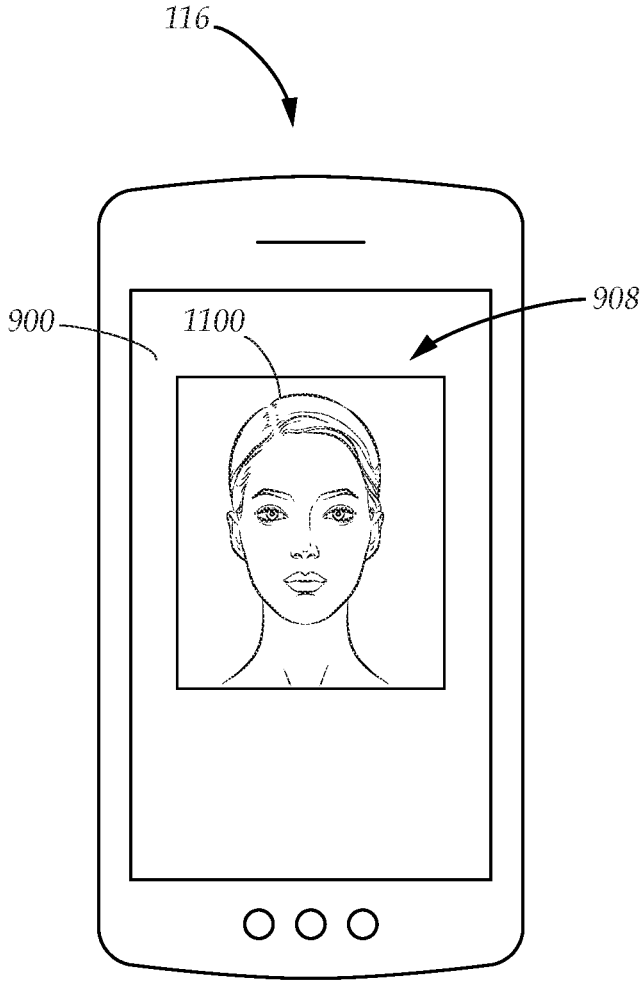
FIG. 11 is a front view of a representative computing device including one embodiment of an apparatus configured to receive an image of the user as input in accordance with certain embodiments of the disclosure.

In some embodiments, the UV radiation exposure moni- toring apparatus 104 generates a plurality of selectable answers that the user 400 may select as input 908a-908d in response to the query 906. In other embodiments, as shown in FIG. 11, the UV radiation exposure monitoring apparatus 104 is configured to receive from the user 400 one or more images 1100 of various physical characteristics as input 908a-908d.

In some embodiments, the questionnaire 904 includes one or more queries 906 regarding markers related to genetic conditions and/or the user's 400 predisposition to erythemal reddening, sun damage, skin cancer, and/or the like. In some embodiments, such queries 906 facilitates a full understand- ing of the user's 400 skin, genetics, and/or likelihood of developing sun-related damage. In some embodiments, the genetic queries 906 are used to capture a base condition of the user 400 prior to their use of sunscreen, protective wear, and/or the like. In some embodiments, input 908a-908d provided in response to these queries 906 are weighted more heavily that input 908a-908d provided in response to other queries 906 due to the fact that genetic factors are incredibly important in determining the user's 400 skin type.

In some embodiments, each query 906 will include a unique weight, which may be determined on a sliding scale. For example, if the user 400 is asked "What is the color of your skin?", the query 906 may include an increased weight when determining the user's 400 skin type than a query 906 regarding the natural color of the user's 400 hair since there is general understanding that, while natural hair color is an important factor in skin type, overall, skin color is more determinative of skin type.

In some embodiments, input 908a-908d provided in response to each query 906 is also weighted. For example, if the user 400 is asked "What is the color of your eyes?", input 908a-908d indicating the answer choice of "Light Blue" may be weighted more heavily than input 908a-908d indicating "Dark Brown or Black", since users 400 with darker complexion and features are less likely to have severe reactions to UV radiation exposure. In these and other embodiments, if an answer option indicates the user 400 is more likely to suffer damage from minimal UV exposure, such input 908a-908d may be given greater weight than an answer option indicating that the user 400 is less susceptible to UV damage.

In some embodiments, at least a portion of the questionnaire 904 is directed to habits of the user 400 to further understand how the user 400, given their skin type, operates on a day-to-day basis. Some of these queries 906 may relate to sunscreen use, level of SPF typically used, frequency of protective-wear use, activities the user participates in, and/or the like. In some embodiments, the questionnaire 904 further includes queries 906 relating to occupation, medical treatment, and/or the like.

In some embodiments, the questionnaire 904 is presented to the user 400 intermittently or periodically over the life of the UV light sensor assembly 102 and the input 908a-908d is updated accordingly.

In some embodiments, queries 906 are presented in multiple tiers. For example, if a user 400 is asked "How frequently do you wear sunscreen while participating in an outdoor activity?" and the user 400 selects "Always" or "Frequently", a follow-up question may be asked regarding a level of SPF typically used. In some embodiments, these tiered queries 906 enable the UV radiation exposure monitoring apparatus 104 to first understand the user's 400 habits, and, second, understand the integrity or extent of that habit, to ensure maximum accuracy in calculating their UV exposure threshold.

In one embodiment, a tiered query 906 may regard skin conditions, procedures such as a facial or chemical peel, and/or medications that impact photosensitivity. In this manner, the UV radiation exposure monitoring apparatus 104 identifies any health-related factors impacting a user's 400 UV exposure threshold, as described in more detail below.

In some embodiments, the UV radiation exposure monitoring apparatus 104 may present to the user 400 queries 906 related to occupation. For example, if a user 400 400 provides input 908a-908d indicating participation in an occupation that requires work outside such as construction, field work, gardening, or any other outdoor labor or occupation, this information may be factored into a maximum UV radiation exposure threshold 1200 for the user 400, as discussed in more detail with reference to FIG. 12 below.

In some embodiments, the physical characteristic input 908a-908d is used to determine the user's 400 Fitzpatrick Skin Type, a recognized dermatological scale used to assess an individual's photosensitivity and erythemal qualities. In one embodiment, the questionnaire 904 includes a series of ten (10) queries 906 regarding the user's 400 physical attributes and previous experience with sun exposure or overexposure that will allow an application-housed algorithm to determine the user's 400 Fitzpatrick Skin Type. For example, the user 400 may be asked to identify their eye color from a range of visual input 908a-908d options. Another query 906 might ask the user to identify the severity of their previous sunburns and results therefrom. Input 908a-908d provided in response to the questionnaire 904 may indicate a Fitzpatrick Skin Type that ranges from "Skin Type 1", corresponding to the lightest and most potentially photosensitive skin, to "Skin Type 6", corresponding to the most melanated and least potentially photosensitive skin. In some embodiments, this scale is altered to include half-step skin types for Types 1-3 to account for users 400 who are in-between skin types, thereby allowing for a more accurate assessment of a user's maximum UV exposure threshold.

In some embodiments, the queries 906 allow the user 400 to choose from multiple visual input 908a-908d options, thereby increasing a likelihood of obtaining accurate results. Each question-and-answer combination may be separately weighted to achieve a photosensitivity score for the user 400. In some embodiments, a Fitzpatrick Skin Type is assigned to the user 400 based on this score. The results of the questionnaire 904 may be further enforced using an artificial intelligence (AI) component or module 1404, as discussed in more detail with reference to FIG. 14 below.

Figure 14:
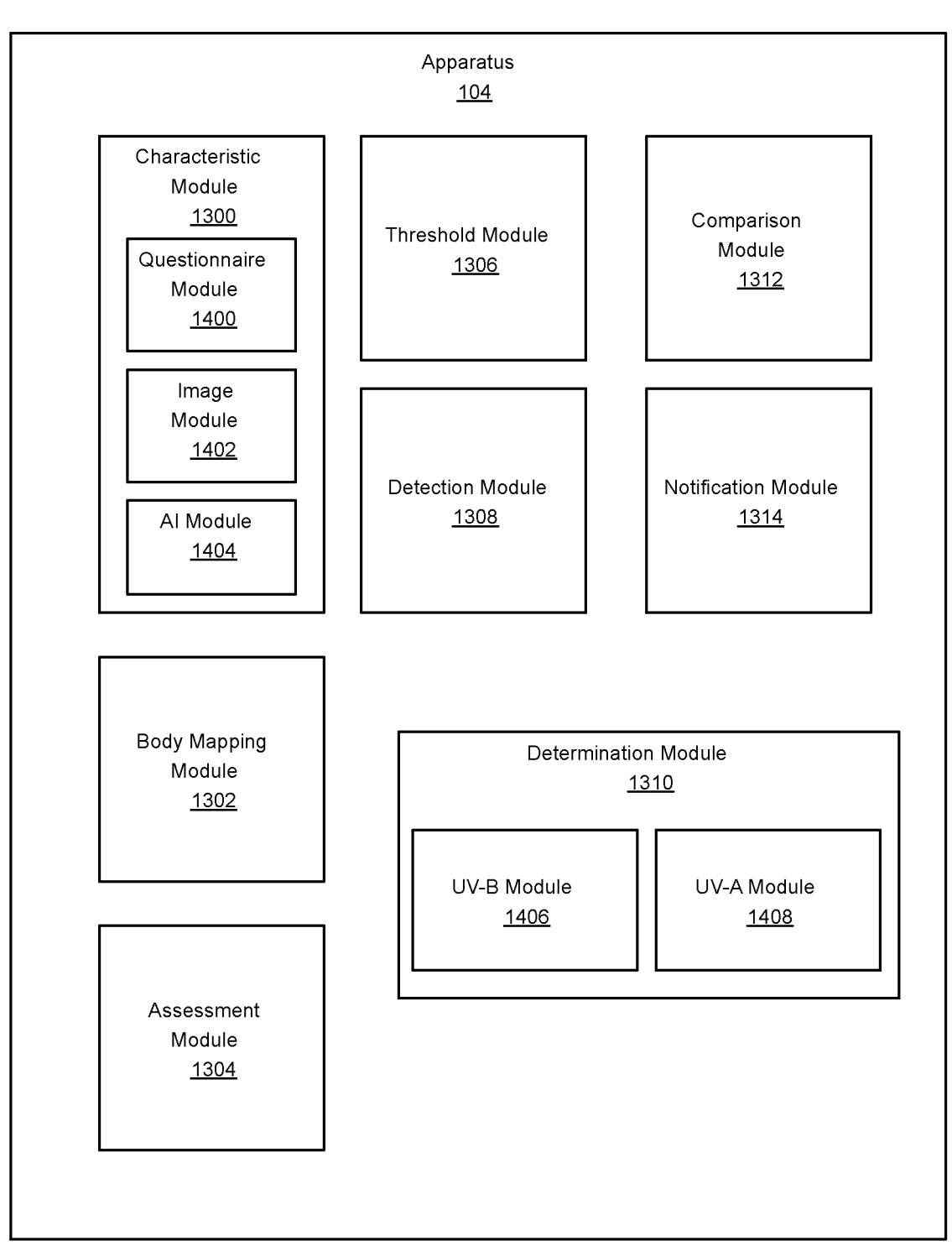
FIG. 14 is a schematic block diagram of another embodiment of a UV radiation exposure monitoring apparatus including various modules in accordance with certain embodiments of the disclosure.

Referring now to FIG. 14 while still referring to FIGS. 11 and 1, for example, in some embodiments, the UV radiation exposure monitoring apparatus 104 is configured to provide solutions to potential "human error" that may occur when determining the user's 400 Fitzpatrick Skin Type. For example, if the user 400 encounters a query 906 that asks them to determine the natural color of their hair or eyes and they are unsure how to answer due to a limited range of options available, or false understanding of the true hue of the feature, the UV radiation exposure monitoring apparatus 104 may utilize the AI module 1404 to inform and/or reinforce the results of the input 908a-908d for determining the user's 400 Fitzpatrick Skin Type.

In some embodiments, the AI module 1404 may request additional imaging or scanning of the user's 400 face since the human face and neck are known to be the most photosensitive regions of the integumentary system. In some embodiments, the AI module 1404 is configured to analyze key physical attributes of the user 400, including, but not limited to, the user's 400 skin color (non-exposed), eye color, the user's 400 tendency to freckle, and more. In some embodiments, the AI module 1404 is implemented following completion of the questionnaire 904 and may require prior consent from the user 400. Upon completion of the facial scan, the data received may be quantified and corroborated with the data received from the user's 400 completion of the Fitzpatrick Skin Type questionnaire 904. In the event additional information is needed from the user 400, the UV radiation exposure monitoring apparatus 104 may present the user 400 with further questions and/or the AI module 1404 may request additional imaging and/or facial scan reinforcement, for example.

In some embodiments, the UV radiation exposure monitoring apparatus 104 is configured to receive from the UV light sensor assembly 102 current UV radiation level input including a current UV radiation level and an exposure time corresponding to at least one area 804 of the user's 400 body 802. In some embodiments, the UV radiation exposure monitoring apparatus 104 generates body mapping data 800 for the user 400 based on the physical characteristic input 908a-908d and/or the current UV radiation level input 908a-908d, as discussed above with reference to FIG. 8.

Figure 10:
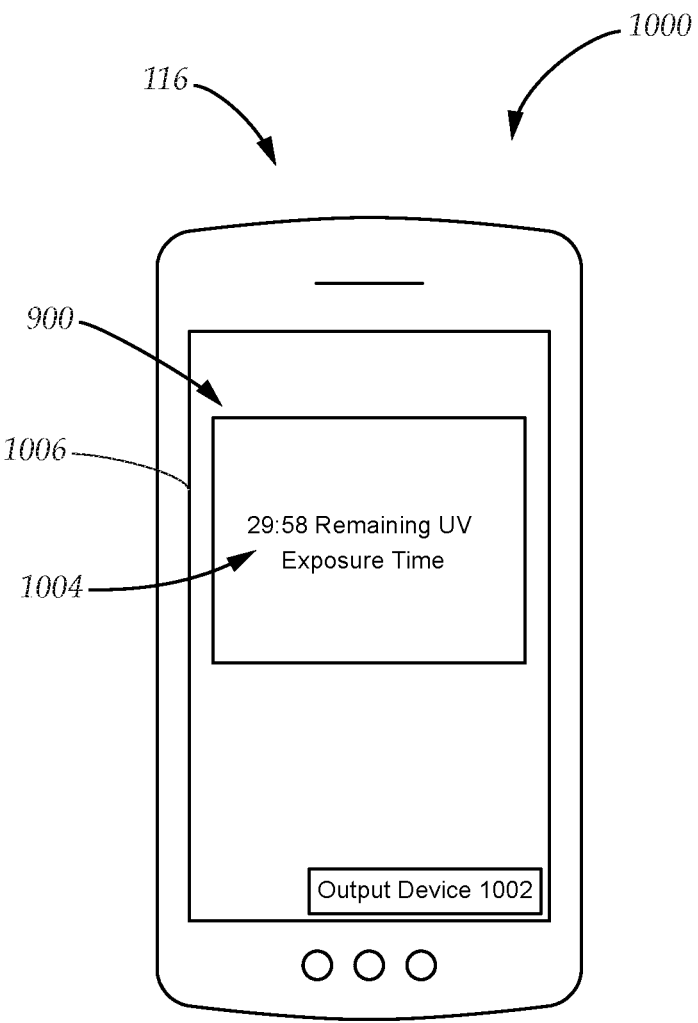
FIG. 10 is a front view of a representative computing device including one embodiment of a display element configured to display a remaining time for safe UV radiation exposure in accordance with some embodiments of the disclosure.

Referring now to FIG. 10, while still referring to FIGS. 1, 8, and 9, in some embodiments, the processor 108 of the UV radiation exposure monitoring apparatus 104 is configured to assess a UV exposure risk for each of area 804 of the user's 400 body 802 based on the physical characteristic input 908a-908d, the current radiation level input 908a-908d, and the body mapping data 800. The UV radiation exposure monitoring apparatus 104 may be further configured to determine, based on the UV exposure risk, a threshold UV radiation exposure value for each of the plurality of areas 804. A current UV radiation exposure value for the at least one area 804 may be determined based on the current UV radiation level and the exposure time. In some embodiments, the current UV radiation exposure value is compared to the threshold UV radiation exposure value for the at least one area 804 to generate UV radiation exposure data based thereon.

In some embodiments, the UV radiation exposure monitoring apparatus 104 includes a notification system 1000 configured to notify the user 400 of a remaining time 1004 for safe UV radiation exposure based on the UV radiation exposure data. In some embodiments, the notification system 1000 is configured to display on the display element 900 the remaining time 1004 for safe UV radiation exposure for one or more areas 804 of the user's 400 body. In some embodiments, the notification system 1000 is configured to alert the user 400 to potential overexposure to UV radiation in one or more areas 804 via an output device 1002. In some embodiments, the output device 1002 may be configured to produce, for example, an auditory alarm, haptic feedback, a visual notification, and/or the like.

Figure 12:
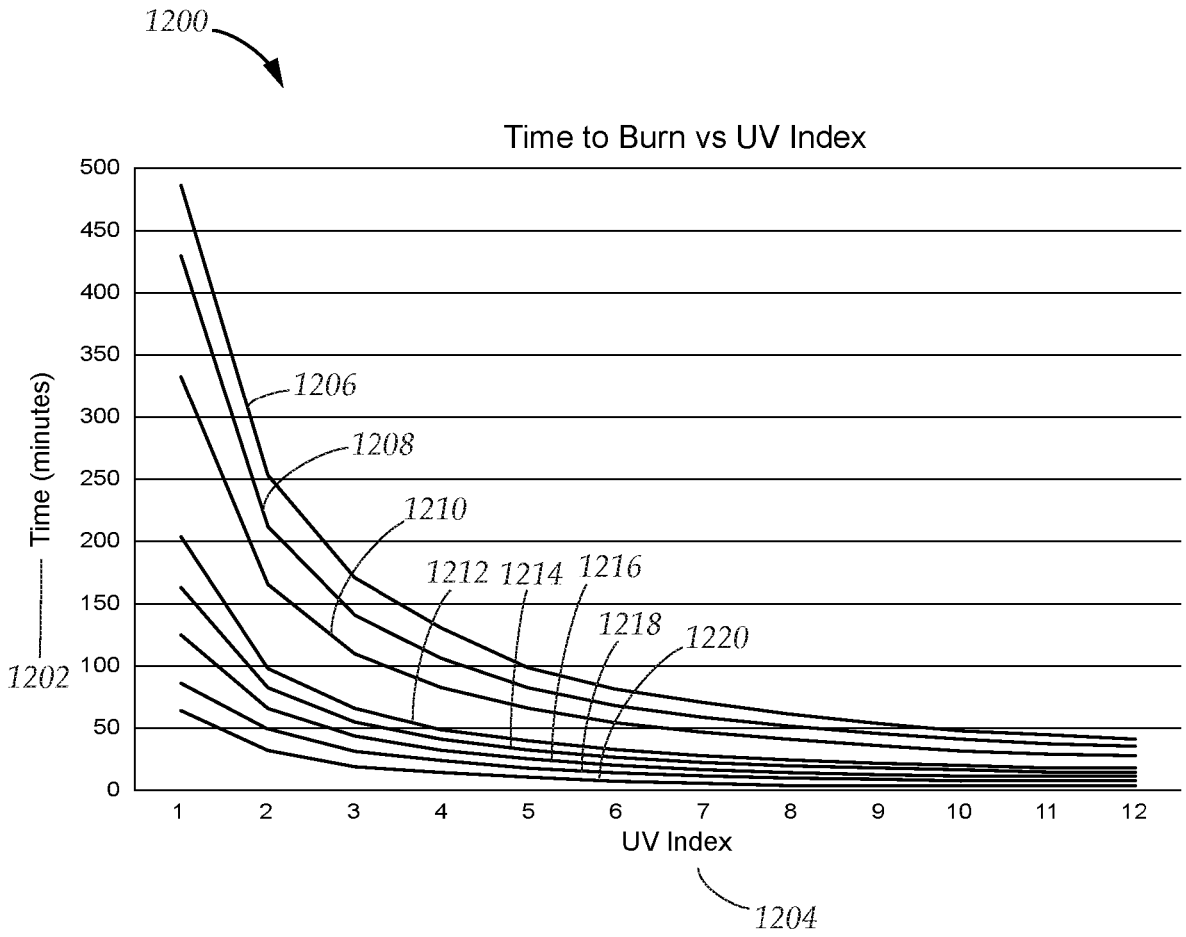
FIG. 12 is a plot graph illustrating a time for safe UV radiation exposure relative to a current UV index for use in accordance with some embodiments of the disclosure.

Referring now to FIG. 12, in some embodiments, the UV radiation exposure monitoring apparatus 104 determines a remaining time 1202 for safe UV radiation exposure based on solar index (SI) dose limits 1200, or maximum UV radiation exposure thresholds 1200, that prevent erythemal reddening based on a predetermined Fitzpatrick Skin Type. FIG. 12 illustrates a summary of data points from various studies and figures that have been interpolated and extrapolated to determine a maximum UV exposure time 1202 based on an established UV index value 1204.

In some embodiments, the maximum amount of time a user 400 can spend under a prolonged, constant level of UV radiation, or maximum UV exposure time 1202, can be represented by the equation MaxTime=C*SI$^a$, where MaxTime is the maximum time 1202 in minutes and C represents the maximum UV radiation exposure threshold 1200. This equation incorporates an extrapolated and dermatologist-verified variable for a Fitzpatrick Skin Type's specific erythemal reaction, multiplied by the current solar index dose limit 1202 (converted from energy readings) to the power of coefficient 'a'.

The coefficient 'a' is approximately −1.0 for all skin types, while C depends on a determined Fitzpatrick Skin Type. Given that 'a' is approximately −1.0 for all skin types, the maximum time 1202 can be multiplied by the SI reported via one data transmission to calculate C, representing the UV dose limit 1200 for reddening or burning for each Fitzpatrick Skin Type. It should be noted that SI multiplied by time is directly related to Joules and the accumulation of SI multiplied by time is proportional to total UV Joules incident on the skin. The net result is an maximum UV radiation exposure threshold 1200, C, for each of the Fitzpatrick Skin Types. As shown in FIG. 12, a maximum UV radiation exposure threshold 1200 is highest at any UV index value 1204 for skin type 6 1206, with increasingly reduced UV index values 1204 from skin type 5 1208 to skin type 4 1210, to skin type 3 1212, to skin type 2.5 1214, to skin type 2 1216, to skin type 1.5 1218 to skin type 1 1220, where skin type 1 1220 includes the lowest maximum UV radiation exposure threshold 1200 at any UV index value 1204.

In some embodiments, although a user 400 is assigned a set skin type value (e.g., Skin Type 3 1212) on the Fitzpatrick scale, this is solely for the user 400 to have a better understanding of where they are represented on the scale. In some embodiments, the official skin type used by the UV radiation exposure monitoring apparatus 104 to configure the maximum UV radiation exposure thresholds 1200 may include something more similar to Skin Type 2.683, for example, such that the UV radiation exposure monitoring apparatus 104 is configured to determine a maximum UV radiation exposure threshold 1200 for the user 400 with extreme accuracy.

Figure 13:
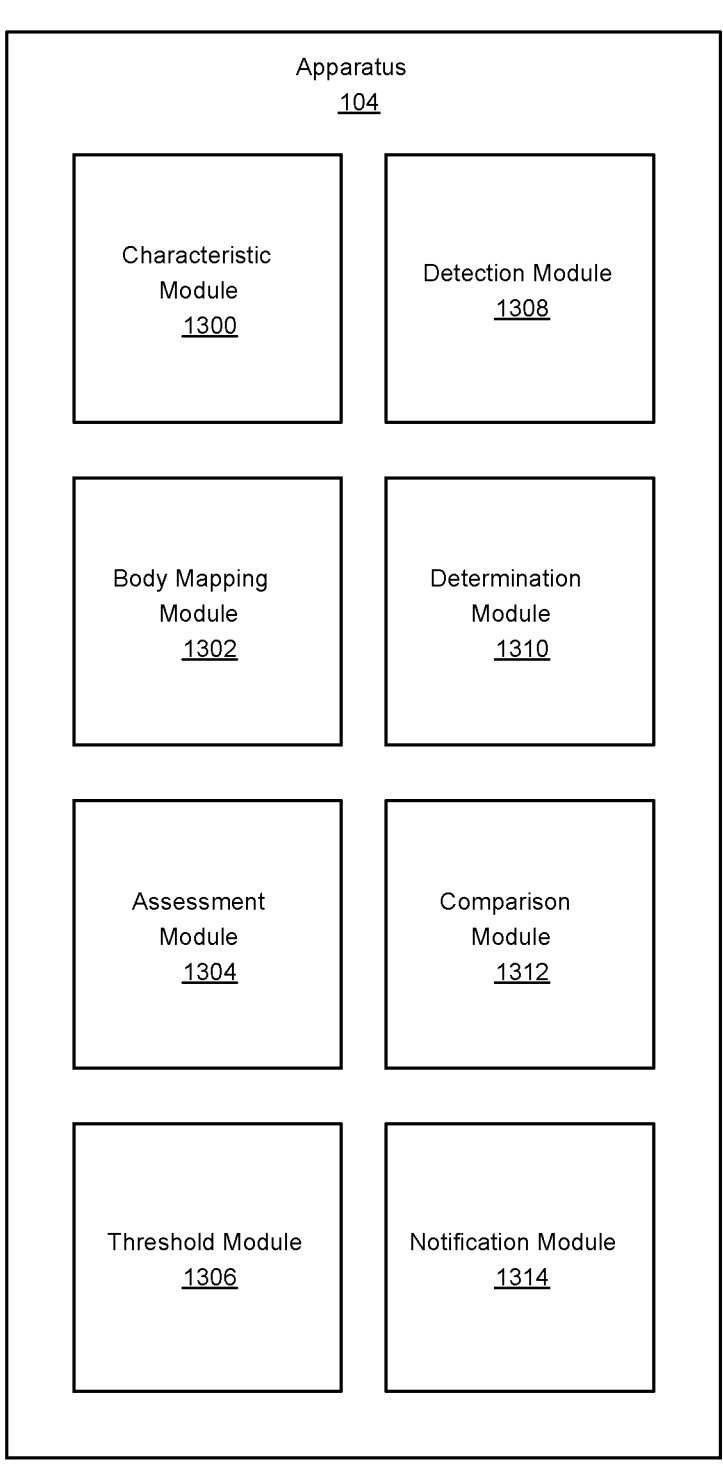
FIG. 13 is a schematic block diagram of a UV radiation exposure monitoring apparatus including various modules in accordance with some embodiments of the disclosure.

Referring now to FIG. 13, while also referring to FIG. 1, the UV radiation exposure monitoring apparatus 104 may include one or more processors 108 and non-transitory computer-readable storage media storing code executable by the processors 108 to perform operations. In some embodiments, the UV radiation exposure monitoring apparatus 104 includes a characteristic module 1300, a body mapping module 1302, an assessment module 1304, a threshold module 1306, a detection module 1308, a determination module 1310, a comparison module 1312, and a notification module 1314.

In some examples, the characteristic module 1300 is configured to receive input 908a-908d from the user 400. In some examples, the input 908a-908d includes one or more characteristics of the user 400. The characteristics include, for example, physical and/or genetic characteristics. In some examples, the characteristics include health and/or family history, such as a personal and/or family history of skin disease, sunburn, skin damage, and/or skin cancer. In some examples, the characteristics include prior activity of the user 400, such as previous sun exposure or a length of time that the user 400 has been exposed to sunlight that day prior to activating and/or utilizing the UV light sensor assembly 102. In some examples, the input 908a-908d includes input 908a-908d received as responses to queries 906 in a questionnaire 904 via a user input device 902, such as the inputs 908a-908d shown in FIG. 9. In some examples, the characteristics include characteristics used to determine the user's 400 Fitzpatrick Skin Type.

In some examples, the characteristics module 1300 is further configured to receive input 908a-908d regarding the user's 400 regular habits, including: habitual protective measures (e.g., sunscreen, covering, etc.), tanning bed use, level of SPF typically used, frequency of protective measures, medication use (e.g., medications that impact photosensitivity), medical and/or cosmetic procedures (e.g., procedures that impact photosensitivity, such as facials or chemical peels), occupation (e.g., an indoor occupation vs. an outdoor occupation, such as agriculture and/or construction), and/or any combination thereof.

In some examples, the characteristics module 1300 is configured to store different profiles including different characteristics for different users 400. For example, the characteristics module 1300 may store a profile for a user 400 and an additional profile for a family member of the user 400, based on that family member's characteristics.

In some examples, the body mapping module 1302 is configured to receive and/or generate body mapping data 800 for the user 400. In some examples, the body mapping data 800 is generated by the apparatus 104 (e.g., by a processor 108 of a computing device 116). In some examples, the body mapping data 800 includes a susceptibility for damage due to UV exposure for skin in a particular area 804 and/or at a particular point of the user 400's body 802. In some examples, the body mapping data 800 includes a location of the UV light sensor assembly 102 on the user 400's body. FIG. 8 illustrates examples of body mapping data 800 for particular users 400a, 400b, 400c. In some examples, the body mapping data 800 includes a risk level that is adjusted and/or generated based at least in part on apparel and/or other protective measures taken by a user 400 in that particular area of their body 802, such as a head covering 700, sunscreen, clothing, and/or any combination thereof.

In some examples, the body mapping data 800 is generated based at least in part on images of the user 400, answers to queries 906, other input 908a-908d from the user 400, and/or any combination thereof. In some examples, the input 908a-908d of the user 400 includes a location of previous skin damage, and the body mapping module 1302 is configured to adjust the body mapping data 800 accordingly. In some examples, the body mapping data 800 includes and/or is generated based on input 908a-908d comprising a visual representation of susceptibility of certain areas 804, such as the visual representations shown in FIG. 8. The visual representation may include, for example, an image file.

In some examples, the assessment module 1304 is configured to assess a UV exposure risk for each of a plurality of areas 804 of the user's 400 body 802 based at least in part on the input 908a-908d received by the characteristics module 1300 and/or on the body mapping data 800 received and/or generated by the body mapping module 1302.

In some examples, the risk assessment module 1304 determines a risk level that is inversely proportional to a numbering of a user's 400 Fitzpatrick Skin type. For example, the characteristics module 1300 determines that a user 400 has type 1 skin (e.g., very pale, white skin, with green or blue eyes), and the risk assessment module 1304 determines that their risk level is high. In another example, the characteristics module 1300 determines that a user 400 has type 6 skin (e.g., dark skin, eyes, and hair), and the risk assessment module 1304 determines that the risk level is relatively low. In some examples, in determining a risk level for the user 400, the risk assessment module 1304 weighs skin color more heavily than other factors.

In some examples, the risk assessment module 1304 determines a different risk level for different areas 804 of the user 400's body 802, according to body mapping data 800. For example, the risk assessment module 1304 determines a low risk level for a foot region 816 of the body 802, particularly if that region 816 is covered by clothing and/or shoes. In some examples, risk assessment module 1304 determines a high risk level for another region 808 that is more exposed and/or tends to be more exposed, such as a user 400's face and/or neck.

In some examples, the risk assessment module 1304 is configured to determine risk levels for different areas of a body 802 via a training process. In a number of examples, the risk assessment module 1304 instructs the user 400 to position themselves in exposure to UV radiation and to place a UV sensor 110 in communication with the risk assessment module 1304, such as one of the UV light sensor assembly 102, in a particular area 804 of their body 802 (e.g., area 808). In some examples, the risk assessment module 1304 then collects data from the UV sensors 110. The risk assessment module 1304 is configured to then, in some examples, instruct the user 400 to place the sensor 110 on a different area 804 of their body 802 (e.g., area 810). In some examples, the risk assessment module 1304 collects data from the UV sensor 110 after the location of the sensor 110 is changed. In some examples, the risk assessment module 1304 is configured to determine relative risks for the different areas 804 (e.g., areas 808 and 810) of the body 802 based on the differences in UV radiation measured by the sensor(s) 110 when placed on those areas 804.

In some examples, the risk assessment module 1304 is configured to assign risk categories to the different areas 804 of the body 802 (e.g., "low risk", "moderate risk", and "high risk"). In some examples, the risk assessment module 1304 is configured to assign the areas 804 of the body 802 a numerical risk value (e.g., a percentage chance of sun damage in a given window of time and/or a numerical value on a scale of 1 to 100).

In some examples, the threshold module 1306 is configured to determine, based at least in part on the UV exposure risk, a threshold UV radiation exposure value for each of the plurality of areas 804. In some examples, the threshold UV radiation exposure is maximum a level of UV radiation exposure which the threshold module 1306 predicts that a particular user 400 will tolerate without significant damage (e.g., sunburn, heat sickness, etc.).

In some examples, the threshold is inversely proportional to the risk determined by the risk assessment module 1304. For example, the risk assessment module 1304 determines that a particular area 808 of a user's 400 body 802 is at high risk due at least in part to lack of coverage in that area 808 and/or a user's 400 characteristics. In such examples, the threshold module 1306 determines a lower threshold value in that area 808 than in another area 816 that benefits from more coverage and thus has a lower risk value, as determined by the risk assessment module 1304.

In some examples, the threshold value for an area 804 in which a UV light sensor assembly 102 is located is proportional to the risk level for that area 804. For example, a sensor assembly 102b located in a high-exposure area, such as a user's chest and/or neck area 808, is likely to detect a higher percentage of the UV radiation that a user's body 802 is being exposed to than a sensor assembly 102 located in a lower-exposure area, such as on a user's feet 816. As such, the threshold value for the higher-risk area 808 is higher than the threshold value for the lower-risk area 816, since the threshold value for the lower-risk area 816 is not as accurate of an indicator of total UV exposure for the user 400 and merits more caution when using it as a generalized indicator of UV exposure.

In some examples, the threshold is in the units of Joules ("J") and/or millijoules ("mJ"). In some examples, the threshold for a particular skin type is proportional to a "time to burn" for that particular skin type, as shown in FIG. 12.

In some examples, the threshold module 1306 is configured to receive a skin type from the characteristics module 1300 and/or determine a skin type based on information from the characteristics module 1300. In some examples, the threshold module 1306 stores baseline threshold values for each of a number of skin types (e.g., each of the Fitzpatrick skin types) and is configured to determine the threshold UV radiation level based at least in part on the skin type. In some examples, the threshold module 1306 assigns a baseline threshold level of 1500-6000 mJ for users with more susceptible skin types. In some examples, the threshold module 1306 assigns a baseline threshold level of 800-1400 mJ for less susceptible skin types.

In some examples, the threshold module 1306 is configured to determine the baseline threshold value for a particular area of the body 802 based at least in part on skin type and/or a risk level for that area 804 and to adjust the baseline threshold value based at least in part on acute characteristics received from the characteristics module 1300. Acute characteristics include mutable characteristic that may vary for a particular user 400 over time. Acute characteristics may include, for example, current skin damage, prior sun exposure, use of products applied to the skin (e.g., sunscreen, antioxidants, moisturizer, aloe vera etc.), clothing worn underneath a UV sensor 110, other coverage for the skin positioned beneath a UV sensor 110, and/or any combination thereof.

For example, in one embodiment, the characteristics module 1300 determines that a user 400 has fair skin. In response, the threshold module 1306 determines a baseline threshold value of 2000 mJ for that area of the user's 400 body 802. However, the threshold module 1306 determines that the user 400 has applied sunscreen to the relevant area(s) 804 and has a slight tan from moderate prior sun exposure but does not have any burns. In response, the threshold module 1306 increases the dose from the baseline threshold of 2000 mJ to a more accurate threshold value of approximately 2500 mJ, since the skin will not be exposed to all of the UV radiation picked up by a sensor 110 in that area (i.e., due in part to the sunscreen blocking some of that radiation).

In some examples, the threshold value reflects an estimated maximum level of UV radiation that could be detected via a UV sensor placed on a particular portion of the body 802 without the user 400 experiencing skin damage, which may be higher than a level of UV radiation that would harm the user 400 without the presence of certain acute characteristics (e.g., sunscreen, clothing, etc.). In some examples, the threshold module 1306 weighs genetic factors received from the characteristics module 1300 (e.g., eye color, skin color, etc.) more heavily than other factors, such as acute characteristics and/or habits.

In some examples, the display element 900 displays a graphical user interface ("GUI") with a "toggle" element for the user 400 to input acute characteristics. For example, if the user 400 has applied sunscreen prior to initializing the device or if the user is wearing protective gear prior to initializing the device, the user 400 could switch these options to "ON" via the toggle elements.

In some examples, the detection module 1308 is configured to detect UV radiation incident on a sensor 110 associated with the user 400. In a number of examples, the detection module 1308 is configured to detect, via a wearable UV light sensor 110, a current UV radiation level and/or an exposure time corresponding to at least one of the plurality of areas 804 for which the threshold module 1306 determined a threshold value.

In some examples, the UV sensing assembly 102 sends UV detection data to the monitoring apparatus 104 in packets of data. In some examples, the detection module 1308 is configured to receive, accumulate, process, and/or store this data.

In some examples, the at least one area 804 is an area 804 in which the UV light sensor 110 is located. In some examples, the UV light sensor 110 is part of a UV light sensor assembly 102 that is configured to be worn by the user 400 at one or more areas 804 of their body 802. For example, as shown in FIG. 8, the UV light sensor assembly 102*a* is located in a forearm area 812. In some examples, the UV light sensor assembly 102*b* is located in a neck/upper chest area 806. In some examples, the UV light sensor assembly 102*c* is located on a helmet 700 worn by a user 400*c*. In some examples, the UV light sensor assembly 102 is located on an upper arm area of the user 400*c*.

In some examples, the detection module 1308 is communicative with the sensor 110 and/or the UV radiation assembly 102. In some examples, the detection module 1308 is configured to detect the UV radiation at periodic intervals. In some examples, the detection module 1308 is configured to poll the UV sensor 110 periodically. In some examples, the detection module 1308 is configured to poll the UV sensor 110 at a period in a range between about thirty (30) seconds and about five (5) minutes.

In some examples, the detection module 1308 is configured to detect an exposure time for at least one area 804 of the body 802. In some examples, the exposure time includes a total length of time which has passed since an initial time beginning the period of UV exposure and the current time. In some examples, the initial time is determined based at least in part on input 908*a*-908*d* from the user 400. In some examples, the user 400 selects a "start" option displayed on the display element 900 via a user interface. In some examples, the user 400 inputs a time at which they began their sun exposure. In some examples, the initial time is a time of day at which the detection module 1308 first detects UV radiation via the UV sensor 110.

In some examples, the detection module 1308 is configured to separately detect UV-A radiation and UV-B radiation. In some examples, the detection module 1308 is configured to update a visual display (e.g., via the display element 900) to show the detected radiation. In some examples, the detection module 1308 is configured to present a display showing a user 400's body 902, as shown in FIG. 9. In some examples, as the detection module 1308 receives data on UV exposure, the detection module 1308 continuously updates the display to reflect areas 804 of the user's body 902 that have been exposed to UV radiation. In some examples, updating the display includes darkening and/or otherwise changing a color of a portion of a visual representation of the user's 400 body 802 on the display 902. In some examples, the detection module 1308 updates the display 902 based at least in part on a type of UV radiation detected (e.g., UV-A and/or UV-B). Since UV-B radiation can be more immediately damaging to a user 400's skin, in some examples, the detection module 1308 weighs UV-B radiation more heavily when updating the display.

In some examples, based on the characteristics of the user 400, the monitoring apparatus 104 is configured to determine four levels of accumulation for the user, characterized as basic exposure, intermediate exposure, advanced exposure, and dangerous exposure. In some examples, on a visual display of the user's 400 body 802, these levels coordinate with colors to serve as visual indicators for the user 400 to understand their pathway to reaching maximum UV exposure levels. In some examples, the basic exposure region of a user's 400 identified maximum exposure range coordinates with the color green, intermediate exposure with the color light orange, advanced exposure coordinates with the color red, and dangerous exposure coordinates with the color black. In some examples, these visual indicators can help the user to understand what level of UV exposure they are currently in, based on accumulated UV detection.

In some examples, the determination module 1310 is configured to determine a current UV radiation exposure value for at least one of the plurality of areas 804 of the user's 400 body 802 based on at least one of the current UV radiation level and/or the exposure time received from the detection module 1308. In some examples, the current UV radiation exposure value reflects a total UV exposure for a particular area 804 of the body 802 over a time period commencing at the initial time. In some examples, the total UV exposure is determined based on an aggregation of one or more measurements received from the UV sensor 110. In some examples, the total UV exposure is determined based on the highest measurement received from the UV sensor 110. In some examples, the total UV exposure is determined based at least in part on measurements from multiple UV sensors 110 positioned on different portions of the body 802. In some examples, the determination module 1310 determines the total UV exposure to be an area 804 under a curve of a graph of UV detection over time.

In some examples, the comparison module 1312 is configured to compare the level of UV exposure determined by the determination module 1310 to the threshold UV radiation exposure value determined by the threshold module 1306. In some examples, the level of UV exposure is determined for a particular area 804 of the body 802 and compared to a threshold value for that area 804.

In some examples, the comparison module 1312 is configured to determine a difference between the current UV radiation exposure value and the threshold UV radiation exposure value. In some examples, the comparison module 1312 is configured to determine whether the current UV radiation exposure value is within a given range of the threshold UV exposure value.

In some examples, the comparison module 1312 is configured to determine that the current UV radiation exposure value is less than the threshold UV exposure value and to determine a remaining time before the UV radiation exposure value is predicted to meet and/or exceed the threshold value. In some examples, the comparison module 1312 predicts the remaining time based at least in part on past measurements from the UV sensor 110, times of past measurements from the UV sensor 110, characteristics from the characteristic module 1300, acute characteristics, and/or any combination thereof.

In some examples, the comparison module 1312 is configured to predict a remaining time based at least in part on a relationship between a total safe time for UV exposure, a skin type, and a UV index for the user's location, such as those shown in FIG. 12. In some examples, the comparison module 1312 is configured to communicate with weather information provider (e.g., via an application programming interface ("API")) to determine the UV index for the user's 400 location.

In some examples, the comparison module 1312 is configured to generate UV radiation exposure data. In some examples, the UV radiation exposure data includes the current UV radiation exposure and/or a predicted remaining time for safe UV radiation exposure.

In some examples, the notification module 1314 is configured to notify the user 400 of the remaining time for UV radiation exposure based on the UV radiation exposure data. In some examples, the notification module 1314 is configured to notify the user 400 via the computing device 116. In some examples, the notification includes at least one of haptic feedback (e.g., vibrations), sound, a change and/or addition to the display element 900, and/or any combination thereof. In some examples, the notification is similar to the notification shown in FIG. 10.

In some examples, the threshold module 1306 is configured to determine four levels of threshold accumulation for the user 400, characterized as basic exposure, intermediate exposure, advanced exposure, and dangerous exposure. In some examples, the notification module 1314 is configured to notify the user 400 of exposure levels at each threshold shift. In some examples, when the user's 400 exposure accumulation status has surpassed the basic exposure range and has entered the intermediate exposure range, the notification module 1314 notifies the user 400. In some examples, the notification module 1314 is configured to determine a notification frequency based at least in part on changes in the remaining time. In some examples, notification frequency is customizable by the user 400. In some examples, the notification module 1314 is configured to notify the user 400 more frequently given the amount of time adjusted to remain for the user's 400 activity.

In some examples, the notification module 1314 is configured to use methods of machine learning to find the ideal moments during a user's 400 UV exposure session to notify them. In some examples, the notification module 1314 is configured to, after a UV exposure session has ended, display a graph summarizing actual UV exposure over time during the period of use based at least in part on measurements received from the detection module 1308.

In some examples, the UV radiation exposure monitoring apparatus 104 is configured to enable a user 400 to select points of time along that graph at which they determined they may have felt at risk of developing sun damage. In some examples, the UV radiation exposure monitoring apparatus 104 is configured to further enforce these inputs by asking a user 400 post-activity-questions, such as if the user 400 experienced any erythemal reddening following use of the UV sensor 110, when the reddening occurred and where, as well as additional qualitative and quantitative inquiries. In some examples, the threshold module 1306 is configured to adjust the user's 400 maximum exposure threshold based at least in part on these inputs. In some examples, the notification module 1314 is configured to adjust the frequency in which the user 400 is notified based at least in part on these inputs. In some examples, the UV radiation exposure monitoring apparatus 104 is configured to store these inputs over time for multiple sessions of UV exposure and to employ a machine learning method to determine threshold levels and/or how frequently to notify a user 400.

Referring now to FIG. 14, in some embodiments, the UV radiation exposure monitoring apparatus 104 further includes a questionnaire module 1400, an image module 1402, an AI module 1404, a UV-B module 1406, and a UV-A module 1408.

In some examples, the characteristic module 1300 includes the questionnaire module 1400. In some examples, the questionnaire module 1400 is configured to generate a questionnaire for the user 400 regarding their physical characteristics, as shown in FIG. 9. In some examples, the input 908*a*-908*d* received by the characteristics module 1300 includes input 908*a*-908*d* received from the user 400 in response to the questionnaire 904. In some examples, the questionnaire 904 includes at least one of a user's 400 hair color, a user's 400 skin color, a user's 400 eye color, the presence of freckles, how the user's 400 skin typically reacts to sun exposure (e.g., burning, blistering, tanning), the degree to which the user 400 tans (e.g., never tans to tans deeply), how sensitive the user's 400 face is to the sun, the amount of recent sun exposure the user 400 has had, whether they intentionally tan or expose themselves to sun for cosmetic reasons, and/or any combination thereof.

In some examples, the characteristic module 1300 includes the image module 1402. In some examples, the input 908*a*-908*d* received by the characteristic module 1300 includes an image of at least one physical characteristic of the user 400. As shown in FIG. 11, in some examples, the image is an image of the user's 400 face. In some examples, the image is taken via a camera of the input device 902 and/or uploaded from the input device 902.

In some examples, the image module 1402 is configured to analyze the image to determine a skin type for the user 400. In some examples, the image module 1402 is configured to derive characteristics from the image (e.g., eye color, skin color, hair color).

In some examples, the characteristic module 1300 includes an artificial intelligence (AI) module 1404. In some examples, the AI module 1404 is configured to analyze an image received by the image module 1402 to determine characteristics of the user 400. In some examples, the AI module 1404 is configured to use techniques such as Convolutional Neural Networks (CNNs), Support Vector Machines (SVMs), Local Binary Patterns (LBPs), and/or any combination thereof. In some examples, the AI module 1404 trained on training data that includes various images of different users 400 with different skin types and characteristics. In some examples, the AI module 1404 determines a skin type for the user 400 by analyzing the image of the user 400. In some examples, the AI module 1404 is further configured to determine a threshold UV exposure for the user 400 based on the image. In some examples, the AI module 1404 is trained on images of other users 400 and threshold UV exposures for those users 400. In some examples, the threshold module 1306 determines the threshold for the user 400 based at least in part on input from the AI module 1404.

In some examples, the AI module 1404 compares the features of the user 400 against a database of known characteristics associated with different skin types and/or levels of photosensitivity. In some examples, this database is a training database.

In some examples, the AI module 1404 scans a portion of the user's 400 body 802, such as their face, in addition to or in alternative to capturing an image of the user 400. Examples of inputs used by the AI module 1404 to determine a skin type include, but are not limited to skin color, eye color, freckles, and/or any combination thereof.

In some examples, the AI module 1404 is configured to correlate collected data from the scan and/or image with responses to the user's 400 questionnaire 904. In some examples, the AI module 1404 is configured to generate additional queries 906. In some examples, the characteristics module 1300 is configured to determine discrepancies between answers to queries 906 and features detected by the AI module 1404 and to update user characteristics based at least in part on input from the AI module 1404.

In some examples, the AI module 1404 is configured to determine a current level of skin damage, and the threshold module 1306 is configured to adjust (e.g., lower) the threshold based at least in part on this skin damage. In some examples, the AI module 1404 is configured to prompt the user 400 to scan their face before sun exposure and after sun exposure. In various examples, the AI module 1404 is configured to determine changes in the user's 400 features by comparing these scans. In some examples, the AI module 1404 detects skin damage between the before and after scans, and the threshold module 1306 uses this skin damage and the threshold value used during that period of exposure to update a machine learning module for determining the threshold value.

In some examples, the AI module 1404 is trained to detect skin damage and/or other dermatological features based on training data that includes images of dermatological features and/or skin damage. Such dermatological features include, for example: moles, freckles, skin texture, scars, signs of previous sun damage, masses, and/or any combination thereof. In some examples, the AI module 1404 is configured to recognize variations in skin condition by analyzing multiple images and/or scans of the user's 400 skin over time. In some examples, the monitoring apparatus 104 is configured to present such changes in a customized report.

In some examples, the AI module 1404 is configured to use protective measures (e.g., acute characteristics) employed by the user 400 and the variations in skin condition as inputs in a machine learning algorithm. In some examples, the AI module 1404 is configured to use this machine learning algorithm to make recommendations for particular users 400 (e.g., protective coverings, SPF use, etc.) to help mitigate these variations in skin conditions. In some examples, the AI module continuously learns about the user 400 over time and over multiple sessions of UV exposure to provide tailored recommendations for that user 400. In some examples, the AI module 1404 is configured to recommend placement of the sensor assembly 102.

In some examples, the determination module 1310 includes a UV-B module 1406 and/or a UV-A module 1408. In some examples, the determination module 1310 is configured to determine a current level of UV-A exposure and a current level of UV-B exposure. In some examples, the determination module 1310 is configured to modify the total level of current UV exposure by weighing UV-A or UV-B more heavily than the other. In some examples, the determination module 1310 operates under a short-term skin health setting and weighs UV-B more heavily than UV-A, since UV-B is often more likely to cause short-term skin damage, such as sun burns.

In some examples, the determination module 1310 operates under a long-term skin health setting and weighs UV-A more heavily than UV-B, since UV-A rays can penetrate the skin more deeply and may have longer-lasting effects than UV-B rays. In some examples, the UV radiation exposure monitoring apparatus 104 receives input from the user 400 regarding a preference for short term skin health, long term skin health, or both. In some examples, the UV radiation exposure monitoring apparatus 104 receives a preference for short term skin health, and the determination module 1310 weighs the UV-B radiation from the UV-B module 1406 more heavily than the UV-A radiation from the UV-A module 1408. In various examples, the UV radiation exposure monitoring apparatus 104 does not receive a preference from the user 400 and defaults to weighing the UV-B radiation more heavily. In some examples, the UV radiation exposure monitoring apparatus 104 assigns the weights based at least in part on at least one of a family history of skin disease, a personal health history, characteristics from the characteristics module 1300, and/or any combination thereof. For example, if the user 400 indicates that they have a family history of skin cancer, in some examples, the determination module 1310 weighs the UV-A radiation more heavily than the UV-B radiation. In some examples, the UV radiation exposure monitoring apparatus 104 receives input from the user 400 that includes a percentage (e.g., 60% long-term skin health and 40% short-term skin health), and the determination module 1310 weighs the total determined UV-A radiation from the UV-A module 1408 and the total determined UV-A radiation from the UV-B module based at least in part on this percentage. As such, in some examples, the determination module 1310 determines a total UV exposure that is different from the user's 400 actual total UV exposure during that period due to the weighing of different types of UV radiation.

Figure 15:
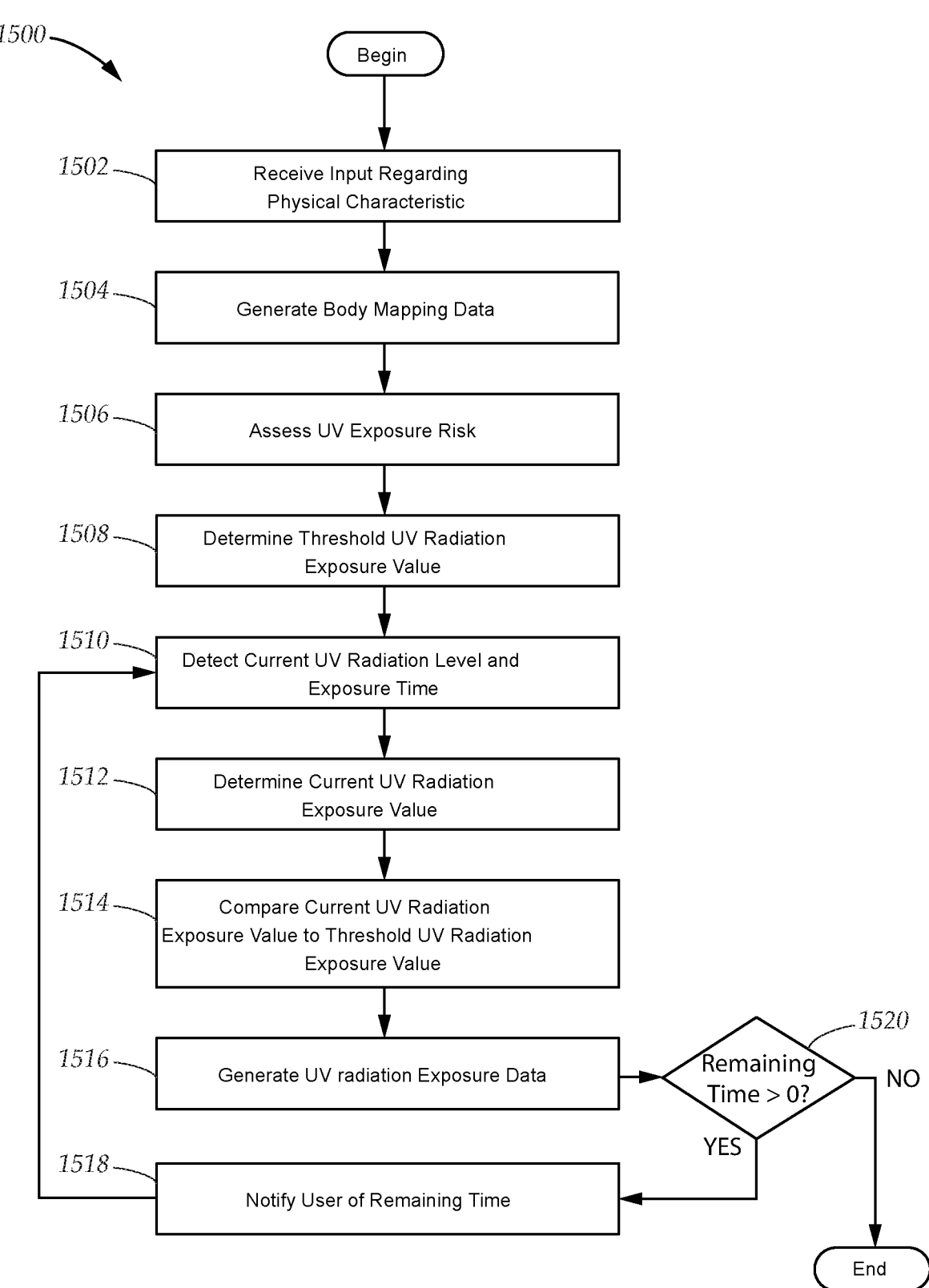
FIG. 15 is a flow chart diagram of one embodiment of a method for monitoring UV radiation exposure and notifying a user of a risk of overexposure in accordance with some embodiments of the disclosure.
Figure 16:
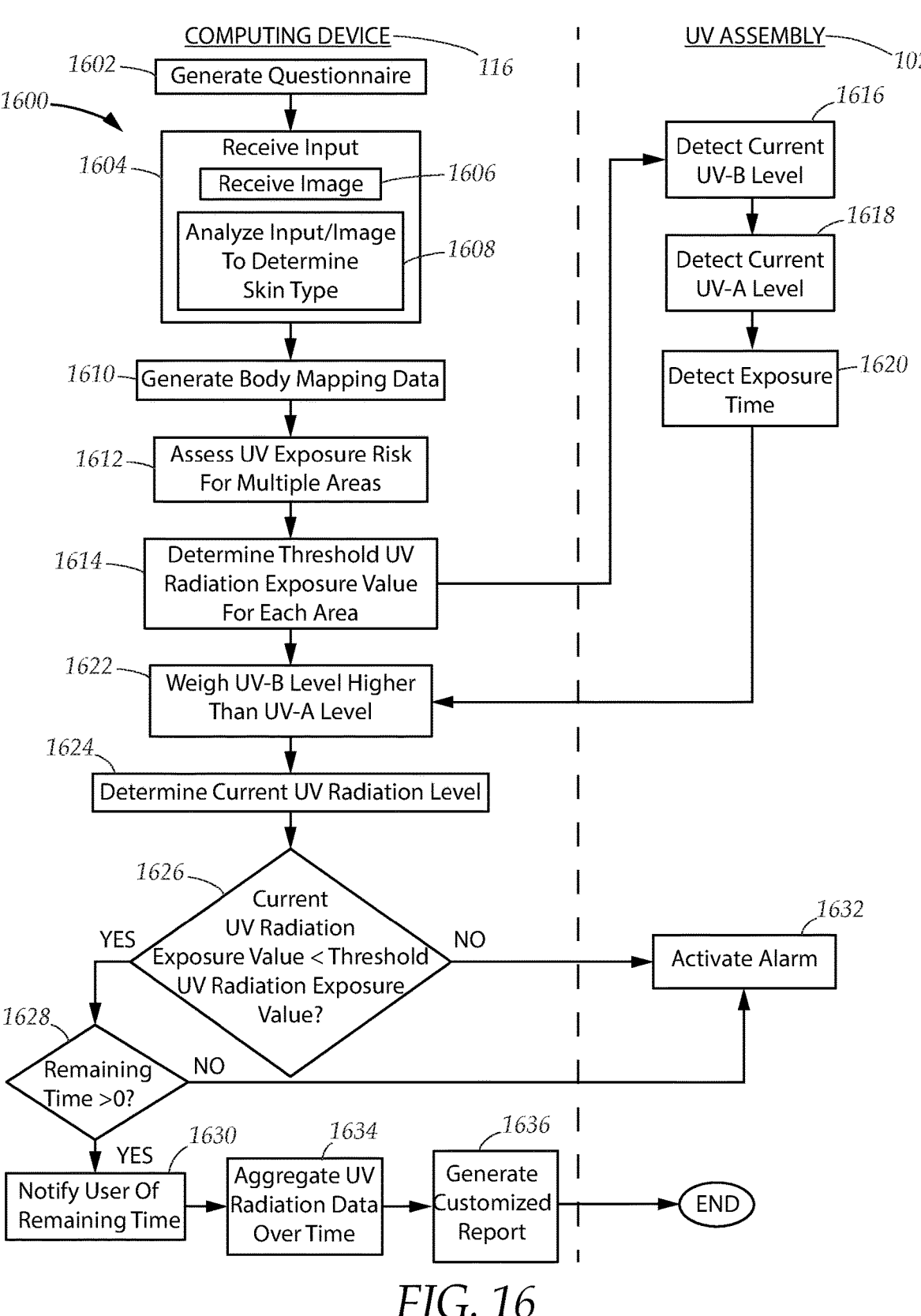
FIG. 16 is a flow chart diagram of another embodiment of a method for monitoring UV radiation exposure and notifying a user of a risk of overexposure in accordance with some embodiments of the disclosure.

Referring now to FIGS. 15 and 16, a method 1500 for monitoring UV radiation exposure and notifying a user 400 of a risk of overexposure includes receiving 1502, by a processor 108, input 908*a*-908*d* including at least one physical characteristic of a user. The method 1500 further includes generating 1504, by the processor 108, body mapping data 800 for the user and assessing 1506, by the processor 108, a UV exposure risk for each of a plurality of areas 804 of the user's body 802 based on the input 908a-908d and the body mapping data 800.

The operations further include determining 1508, based on the UV exposure risk, a threshold UV radiation exposure value for each of the areas 804. In some examples, the method 1500 includes detecting 1510, via a UV sensor 110, a current UV radiation level and exposure time for the at least one of the areas 804. In some examples, the method 1500 includes determining 1512 a current UV radiation exposure value based at least in part on the detecting 1510. In some examples, the method 1500 includes comparing 1514, by the processor 108, the current UV radiation exposure value to the threshold UV radiation exposure value for one or more of the areas 804 and generating 1516 UV radiation exposure data based thereon. In some examples, the method 1500 includes notifying 1518, by the processor 108, the user 400 of a remaining time for UV radiation exposure of the area 804 based on the UV radiation exposure data.

The method 1500 includes determining 1508, based on the UV exposure risk, a threshold UV radiation exposure value for each of the plurality of areas 804. A wearable ultraviolet (UV) light sensor assembly 102 is configured to be worn by the user in at least one of the areas 804 and is used to detect 1510 a current UV radiation level and an exposure time. The exposure time indicates an amount of time that the area 804 has been exposed to UV radiation. The method 1500 further includes determining 1512, by the processor, a current UV radiation exposure value for the area 804 based on the current UV radiation level and the exposure time. The processor 108 compares 1514 the current UV radiation exposure value to the threshold UV radiation exposure value for the area to generate 1516 UV radiation exposure data, including a remaining time of safe UV exposure. The method the queries 1520 whether the remaining time is greater than zero. If yes, the processor 108 notifies the user 400 of the remaining time for UV radiation exposure based on the UV radiation exposure data and returns to detecting 1510 a current UV radiation level and an exposure time.

In some embodiments, the method 1500 includes iteratively detecting the current UV radiation exposure radiation level and the exposure time at predetermined periodic intervals and updating the remaining time for UV exposure based on the detection. In some examples, the method 1500 is performed by one or more of the modules of the UV radiation exposure monitoring apparatus 104.

Referring now to FIG. 16, in some embodiments, a method 1600 for monitoring UV radiation exposure and notifying a user 400 of a risk of overexposure is, in some examples, an embodiment of the method 1600. In some embodiments, some steps of the method 1600 may be performed by the computing device 116, while other steps of the method 1600 may be performed by the UV light sensor assembly 102.

In some embodiments, the method 1600 includes generating 1602 a questionnaire 904, as illustrated in FIG. 9, and receiving 1604 input 908a-908d from the user 400. In some examples, the input 908a-908d includes information provided in response to the questionnaire 904. In some examples, receiving 1604 the input 908a-908d includes receiving 1606 an image, as illustrated in FIG. 11. In some examples, the receiving 1604 the input 908a-908d includes analyzing the input 908a-908d and/or the image to determine a skin type for the user 400.

In some examples, the method 1600 includes generating 1610 body mapping data 800. In some examples, the method 1600 includes assessing 1612 a UV exposure risk for each of multiple areas 804 of a user 400's body 802. In some examples, the method 1600 includes determining 1614 a threshold UV radiation exposure value for each area 804 of the body 802. In some examples, steps 1602-1614 of the method 1600 are performed by a processor 108 of the computing device 116.

In some examples, the method 1600 includes detecting 1616, at a UV sensor 110, a current UV-B level. In some examples, the method 1600 includes detecting, at the UV sensor 110, a current UV-A level. In some examples, the method 1600 includes detecting 1620, at the UV sensor 110, a total exposure time of the user 400 to UV radiation.

In some examples, the method 1600 includes weighing 1622, by a processor 108 of the computing device 116, the current UV-B level higher than the current UV-A level. In some examples, the method 1600 includes determining 1624 a current UV radiation level based at least in part on these detected values and weights.

In some examples, the method 1600 includes determining 1626 whether a current UV radiation exposure value is less than a threshold UV radiation exposure value. If yes, the method 1600 includes determining 1628 whether the time remaining for safe UV radiation exposure is greater than zero. If no, and/or the current UV radiation exposure value is equal to or greater than the threshold UV radiation exposure value, the method 1600 includes activating 1632 an alarm to alert the user 400 to a risk of overexposure. In some examples, activating 1632 the alarm includes activating an alarm of the UV light sensor assembly 102. In other examples, the alarm is activated at the computing device 116.

In some examples, if the time remaining for safe UV radiation exposure is greater than zero, the method 1600 includes notifying 1630 the user 400 of the remaining time. In some embodiments, the user 400 may be notified of the remaining time via the display element 900 of the computing device 116. In some examples, the method 1600 includes aggregating 1634 UV radiation data over time for that user 400 and/or generating 1636 a customized report for the user 400 based on the aggregate data. In some examples, the customized report includes at least one of a total exposure time, total UV radiation exposure, total UV-A radiation exposure, total UV-B radiation exposure, skin type, characteristics, body mapping data, a recommendation for protection from UV radiation exposure, and/or any combination thereof.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for monitoring ultraviolet (UV) radiation exposure and notifying a user of a risk of overexposure, comprising:

receiving, by a processor, input comprising at least one physical characteristic of a user;

generating, by the processor, body mapping data for the user;

assessing, by the processor, a UV exposure risk for each of a plurality of areas of the user's body based on the input and the body mapping data;

determining, based on the UV exposure risk, a threshold UV radiation exposure value for each of the plurality of areas;

detecting, via a wearable ultraviolet (UV) light sensor, a current UV radiation level and an exposure time corresponding to at least one of the plurality of areas, wherein the wearable UV light sensor assembly is configured to be worn by the user in at least one of the plurality of areas, and wherein the exposure time indicates an amount of time that the at least one of the plurality of areas has been exposed to UV radiation;

determining, by the processor, a current UV radiation exposure value for the at least one of the plurality of areas based on the current UV radiation level and the exposure time;

comparing, by the processor, the current UV radiation exposure value to the threshold UV radiation exposure value for the at least one of the plurality of areas and generating UV radiation exposure data based thereon; and notifying, by the processor, the user of a remaining time for UV radiation exposure of the at least one of the plurality of areas based on the UV radiation exposure data.

2. The method of claim 1, further comprising activating, by the processor, an alarm in the event the current UV radiation exposure value exceeds the threshold UV radiation exposure value.

3. The method of claim 1, further comprising generating, by the processor, a questionnaire for the user regarding the at least one physical characteristic.

4. The method of claim 3, wherein receiving the input comprises receiving input from the user in response to the questionnaire.

5. The method of claim 1, wherein the input comprises an image of the at least one physical characteristic.

6. The method of claim 5, further comprising analyzing, by the processor, the image to determine a skin type of the user.

7. The method of claim 1, wherein determining the current UV radiation level comprises detecting a UV-A radiation level and a UV-B radiation level and weighing the UV-B radiation level more heavily than the UV-A radiation level.

8. The method of claim 1, wherein detecting the current UV radiation level comprises iteratively detecting the current UV radiation level at periodic intervals.

9. The method of claim 1, further comprising aggregating the UV radiation exposure data for the user over a predetermined period of time and generating a customized report for the user based thereon, wherein the customized report comprises at least one recommendation for protection from UV radiation exposure.

10. A system for monitoring ultraviolet (UV) radiation exposure and notifying a user of a risk of overexposure, comprising:

a wearable ultraviolet (UV) light sensor assembly configured to detect a current UV radiation level and an exposure time corresponding to at least one of a plurality of areas of a user's body, wherein the UV light sensor assembly is configured to be worn by the user in at least one of the plurality of areas, and wherein the exposure time indicates an amount of time that the at least one of the plurality of areas has been exposed to UV radiation; and a computing device comprising a processor in communication with the wearable UV light sensor assembly, wherein the processor is configured to:

receive input regarding at least one physical characteristic of the user;

receive body mapping data for the user;

assess a UV exposure risk for each of a plurality of areas of the user's body based on the input and the body mapping data;

determine, based on the UV exposure risk, a threshold UV radiation exposure value for each of the plurality of areas;

determine a current UV radiation exposure value for the at least one of the plurality of areas based on the current UV radiation level and the exposure time;

compare the current UV radiation exposure value to the threshold UV radiation exposure value for the at least one of the plurality of areas and generate UV radiation exposure data based thereon; and notify the user of a remaining time for UV radiation exposure of the at least one of the plurality of areas based on the UV radiation exposure data.

11. The system of claim 10, wherein the processor is further configured to activate an alarm in response to the current UV radiation exposure value exceeding the threshold UV radiation exposure value.

12. The system of claim 10, wherein the processor is configured to generate a questionnaire for the user regarding the at least one physical characteristic.

13. The system of claim 12, wherein the input comprises input from the user in response to the questionnaire.

14. The system of claim 10, wherein the input comprises an image of the at least one physical characteristic.

15. The system of claim 10, wherein the wearable UV light sensor assembly comprises an adaptable housing configured for use in at least one of the plurality of areas of the user's body.

16. The system of claim 10, wherein the wearable UV light sensor assembly is further configured to selectively transmit the current ultraviolet (UV) radiation level and the exposure time to the processor.

17. The system of claim 16, wherein the wearable UV light sensor assembly is configured to selectively transmit the current ultraviolet (UV) radiation level and the exposure time to the processor at periodic intervals.

18. The system of claim 10, further comprising a notification system configured to provide to the user at least one of an auditory alarm, haptic feedback, and a visual notification.

19. An apparatus for monitoring ultraviolet (UV) radiation exposure and notifying a user of a risk of overexposure, comprising:

one or more processors; and non-transitory computer-readable storage media storing code, the code being executable by the one or more processors to perform operations comprising:

receiving physical characteristic input comprising at least one physical characteristic of a user;

receiving, from a UV light sensor assembly, current UV radiation level input comprising a current UV radiation level and an exposure time corresponding to at least one of a plurality of areas of the user's body;

generating body mapping data for the user based on the physical characteristic input and the current UV radiation level input;

assessing a UV exposure risk for each of the plurality of areas based on the physical characteristic input, the current UV radiation level input, and the body mapping data;

determining, based on the UV exposure risk, a threshold UV radiation exposure value for each of the plurality of areas;

determining a current UV radiation exposure value for the at least one of the plurality of areas based on the current UV radiation level input;

comparing the current UV radiation exposure value to the threshold UV radiation exposure value for the at least one of the plurality of areas and generating UV radiation exposure data based thereon; and notifying the user of a remaining time for UV radiation exposure of the at least one of the plurality of areas based on the UV radiation exposure data.

20. The apparatus of claim 19, the operations further comprising:

iteratively receiving the current UV radiation level and the exposure time at predetermined periodic intervals; and updating the remaining time for UV radiation exposure based on the receiving.

\* \* \* \* \*